United States Patent [19]

Torrence et al.

[11] Patent Number: 5,677,289
[45] Date of Patent: Oct. 14, 1997

[54] METHOD OF CLEAVING SPECIFIC STRANDS OF RNA AND MEDICAL TREATMENTS THEREBY

[75] Inventors: Paul Torrence, Silver Spring, Md.; Robert Silverman, Shaker Heights; Ratan Maitra, Euclid, both of Ohio; Krystyna Lesiak, Gaithersburg, Md.

[73] Assignees: The Cleveland Clinic Foundation, Cleveland, Ohio; The United States of America, Washington, D.C.

[21] Appl. No.: 458,050

[22] Filed: Jun. 1, 1995

Related U.S. Application Data

[63] Continuation of Ser. No. 123,449, Sep. 17, 1993, Pat. No. 5,583,032, which is a continuation-in-part of Ser. No. 965,666, Oct. 21, 1992, abandoned.

[51] Int. Cl.$^6$ .......................... A61K 31/70; A61K 48/00; C07H 21/00; C12Q 1/68
[52] U.S. Cl. .................. 514/74; 514/46; 514/47; 436/94; 435/6; 435/91.1; 435/199; 435/240.2; 536/24.5; 536/25.2
[58] Field of Search .................. 514/44, 46, 47; 536/24.5, 25.2; 436/94; 435/6, 91.1, 199, 240.2; 395/3, 5, 6, 8, 33, 34, 72

[56] References Cited

PUBLICATIONS

Dialog File 636: IAC Newsletter DB (TM), #02944476—"Conference Coverage (ICAAC) Antisense Drug Stumbles in Early Trial".
R. Weiss, Science News, vol. 139 (Feb. 16, 1991) pp. 108–109.
C. Stein et al., Science, vol. 261 (Aug. 20, 1993) pp. 1004–1012.
M. Johnston et al., Interferon, vol. 3 (1984) pp. 332–334 & ref pages.
P. Defilippi et al., FEBS Letters, vol. 198(2) (Mar. 1986) pp. 326–332.
J. Chebath et al., Nature, vol. 330 (Dec. 10, 1987) pp. 587–588.
E. Uhlmann et al., Chem. Rev., vol. 90 (4) (Jun. 1990) pp. 543–584.
P. Westermann et al., Biomed. Biochem. Acta, vol. 48(1) (1989) pp. 85–93.
B. Tseng et al., Cancer Gene Therapy, vol. 1 (1) (Mar. 1994) pp. 65–71.
D. Krause et al., JBC, vol. 260(16) (Aug. 5, 1984) pp. 9501–9507.
P. Torrence et al., JBC, vol. 263(3) pp. 1131–1139 (1989).
K. Kariko et al., Biochem, vol. 25 (1986) pp. 3730–3736.
D. Wreschner et al., Nature, vol. 289(1981) pp. 414–417.
Y. Li et al., PNAS, vol. 89 (Apr. 1992) pp. 3185–3189.
R. Walder et al, PNAS, vol. 85 (Jul. 1988) pp. 5011–5015.
J. Goodchild et al., vol. 1(3) BioOrganic Chem, (90) pp. 165–187.
P. Miller et al., Anticancer Drug Design (1987) vol. 2, pp. 117–128.

Primary Examiner—Charles C.P. Rories
Attorney, Agent, or Firm—Pennie & Edmonds LLP

[57] ABSTRACT

A method of using a chimeric molecule made up of an antisense oligonucleotide attached to a 2',5'-oligoadenylate molecule to specifically cleave a sense strand of RNA, wherein the antisense oligonucleotide of the chimeric molecule is hybridized to the sense strand of RNA in the presence of 2',5'-dependent RNase.

11 Claims, 12 Drawing Sheets

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

AAAATTTTTT TTTTTTTTTT TT                                22

( 2 ) INFORMATION FOR SEQ ID NO:2:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

AAAATTTTTT TTTTTTTTTT TT                                22

( 2 ) INFORMATION FOR SEQ ID NO:3:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

TCCTGTATGC AGACCCCAAT ATGTTGTTAT                        30

( 2 ) INFORMATION FOR SEQ ID NO:4:

( i ) SEQUENCE CHARACTERISTICS:

(A) LENGTH: 19 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

GTACTACTCC CTGCTTCTG                                              19

(2) INFORMATION FOR SEQ ID NO:5:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GTACTACTCC CTGCTTCTG                                              19

(2) INFORMATION FOR SEQ ID NO:6:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
            (A) NAME/KEY: miscellaneous feature
            (B) LOCATION: 1-4
            (D) OTHER INFORMATION: A is linked by 2',5'-linkage (ix) FEATURE:
            (A) NAME/KEY: miscellaneous feature
            (B) LOCATION: 4
            (D) OTHER INFORMATION: A is linked at 2'end to following
                base through a linker moiety (xi) SEQUENCE DESCRIPTION: SEQ ID NO:6:

AAAAGTACTA CTCCCTGCTT CTG                                        23

(2) INFORMATION FOR SEQ ID NO:7:

(i) SEQUENCE CHARACTERISTICS:

( A ) LENGTH: 23 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
               ( A ) NAME/KEY: miscellaneous feature
               ( B ) LOCATION: 1-4
               ( D ) OTHER INFORMATION: A is linked by 2',5'-linkage ( i x ) FEATURE:
               ( A ) NAME/KEY: miscellaneous feature
               ( B ) LOCATION: 4
               ( D ) OTHER INFORMATION: A is linked at 2'end to following
                    base through a linker moiety ( x i ) SEQUENCE DESCRIPTION: SEQ ID NO:7:

AAAACAGAAG CAGGGAGTAG TAC                                                    23

( 2 ) INFORMATION FOR SEQ ID NO:8:

( i ) SEQUENCE CHARACTERISTICS:
               ( A ) LENGTH: 23 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
               ( A ) NAME/KEY: miscellaneous feature
               ( B ) LOCATION: 4
               ( D ) OTHER INFORMATION: A is deoxyribonucleic linked at 3'end
                    to following base through a linker moiety ( x i ) SEQUENCE DESCRIPTION: SEQ ID NO:8:

AAAAGTACTACTCC CTGCTTCTG                                                     23

( 2 ) INFORMATION FOR SEQ ID NO:9:

( i ) SEQUENCE CHARACTERISTICS:
               ( A ) LENGTH: 21 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
               ( A ) NAME/KEY: miscellaneous feature (B) LOCATION: 1-2
                    (D) OTHER INFORMATION: A is linked by 2',5'-linkage (ix) FEATURE:
                    (A) NAME/KEY: miscellaneous feature
                    (B) LOCATION: 2
                    (D) OTHER INFORMATION: A is linked at 2'end to following
                        base through a linker moiety (xi) SEQUENCE DESCRIPTION: SEQ ID NO:9:

AAGTACTACT CCCTGCTTCT G                                              21

(2) INFORMATION FOR SEQ ID NO:10:

(i) SEQUENCE CHARACTERISTICS:
                    (A) LENGTH: 23 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
                    (A) NAME/KEY: miscellaneous feature
                    (B) LOCATION: 1-4
                    (D) OTHER INFORMATION: A is linked by 2',5'-linkage (ix) FEATURE:
                    (A) NAME/KEY: miscellaneous feature
                    (B) LOCATION: 4
                    (D) OTHER INFORMATION: A is linked at 2'end to following
                        base through a linker moiety (xi) SEQUENCE DESCRIPTION: SEQ ID NO:10:

AAAAGTACTA CTCCCTGCTT CTG                                            23

(2) INFORMATION FOR SEQ ID NO:11:

(i) SEQUENCE CHARACTERISTICS:
                    (A) LENGTH: 25 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
                    (A) NAME/KEY: miscellaneous feature
                    (B) LOCATION: 1-6
                    (D) OTHER INFORMATION: A is linked by 2',5'-linkage (xi) SEQUENCE DESCRIPTION: SEQ ID NO:11:

AAAAAAGTAC TACTCCCTGC TTCTG                                          25

(2) INFORMATION FOR SEQ ID NO:12:

(i) SEQUENCE CHARACTERISTICS:
                    (A) LENGTH: 23 base pairs (B) TYPE: nucleic acid
                    (C) STRANDEDNESS: single
                    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
                    (A) NAME/KEY: miscellaneous feature
                    (B) LOCATION: 1-4
                    (D) OTHER INFORMATION: A is linked by 2',5'-linkage (ix) FEATURE:
                    (A) NAME/KEY: miscellaneous feature
                    (B) LOCATION: 4
                    (D) OTHER INFORMATION: A is linked at 2'end to following
                        base through a linker moiety (xi) SEQUENCE DESCRIPTION: SEQ ID NO:12:

AAAAGTACTA CACCCTGCTT CTG                                        23

(2) INFORMATION FOR SEQ ID NO:13:

(i) SEQUENCE CHARACTERISTICS:
                    (A) LENGTH: 23 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
                    (A) NAME/KEY: miscellaneous feature
                    (B) LOCATION: 1-4
                    (D) OTHER INFORMATION: A is linked by 2',5'-linkage (ix) FEATURE:
                    (A) NAME/KEY: miscellaneous feature
                    (B) LOCATION: 4
                    (D) OTHER INFORMATION: A is linked at 2'end to following
                        base through a linker moiety (xi) SEQUENCE DESCRIPTION: SEQ ID NO:13:

AAAAGTACTT CACCCACCTT CTG                                        23

(2) INFORMATION FOR SEQ ID NO:14:

(i) SEQUENCE CHARACTERISTICS:
                    (A) LENGTH: 23 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iv) ANTI-SENSE: NO (v) FRAGMENT TYPE:

( v i ) ORIGINAL SOURCE:

( i x ) FEATURE:
      ( A ) NAME/KEY: miscellaneous feature
      ( B ) LOCATION: 1-4
      ( D ) OTHER INFORMATION: A is linked by 2',5'-linkage ( i x ) FEATURE:
      ( A ) NAME/KEY: miscellaneous feature
      ( B ) LOCATION: 4
      ( D ) OTHER INFORMATION: A is linked at 2'end to following base through a linker moiety ( x i ) SEQUENCE DESCRIPTION: SEQ ID NO:14:

AAAACAAGTT CACGCACCAA CTG             23

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: miscellaneous feature
        ( B ) LOCATION: 1-4
        ( D ) OTHER INFORMATION: A is linked by 2',5'-linkage ( i x ) FEATURE:
        ( A ) NAME/KEY: miscellaneous feature
        ( B ) LOCATION: 4
        ( D ) OTHER INFORMATION: A is linked at 2'end to following base through a linker moiety ( x i ) SEQUENCE DESCRIPTION: SEQ ID NO:15:

AAAACTACTC CCTGCTTCT                19

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: miscellaneous feature
        ( B ) LOCATION: 1-4
        ( D ) OTHER INFORMATION: A is linked by 2',5'-linkage ( i x ) FEATURE:
        ( A ) NAME/KEY: miscellaneous feature
        ( B ) LOCATION: 4
        ( D ) OTHER INFORMATION: A is linked at 2'end to following base through a linker moiety ( x i ) SEQUENCE DESCRIPTION: SEQ ID NO:16:

AAAACTACTC CCTGCT                                                                                                    16

( 2 ) INFORMATION FOR SEQ ID NO:17:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: miscellaneous feature
        ( B ) LOCATION: 1-4
        ( D ) OTHER INFORMATION: A is linked by 2',5'-linkage ( i x ) FEATURE:
        ( A ) NAME/KEY: miscellaneous feature
        ( B ) LOCATION: 4
        ( D ) OTHER INFORMATION: A is linked at 2'end to following
            base through a linker moiety ( x i ) SEQUENCE DESCRIPTION: SEQ ID NO:17:

AAAACTACTC CCT                                                                                                       13

( 2 ) INFORMATION FOR SEQ ID NO:18:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: miscellaneous feature
        ( B ) LOCATION: 1-4
        ( D ) OTHER INFORMATION: A is linked by 2',5'-linkage ( i x ) FEATURE:
        ( A ) NAME/KEY: miscellaneous feature
        ( B ) LOCATION: 4
        ( D ) OTHER INFORMATION: A is linked at 2'end to following
            base through a linker moiety ( x i ) SEQUENCE DESCRIPTION: SEQ ID NO:18:

AAAACTACTC                                                                                                           10

( 2 ) INFORMATION FOR SEQ ID NO:19:

( i ) SEQUENCE CHARACTERISTICS:
        ( A ) LENGTH: 22 base pairs
        ( B ) TYPE: nucleic acid
        ( C ) STRANDEDNESS: single (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
            (A) NAME/KEY: miscellaneous feature
            (B) LOCATION: 1-4
            (D) OTHER INFORMATION: A is linked by 2',5'-linkage (ix) FEATURE:
            (A) NAME/KEY: miscellaneous feature
            (B) LOCATION: 4
            (D) OTHER INFORMATION: A is linked at 2'end to following
                    base through a linker moiety (xi) SEQUENCE DESCRIPTION: SEQ ID NO:19:

AAAAAAAAA AAAAAAAAA AA                                22

(2) INFORMATION FOR SEQ ID NO:20:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
            (A) NAME/KEY: miscellaneous feature
            (B) LOCATION: 1-4
            (D) OTHER INFORMATION: A is linked by 2',5'-linkage (ix) FEATURE:
            (A) NAME/KEY: miscellaneous feature
            (B) LOCATION: 4
            (D) OTHER INFORMATION: A is linked at 2'end to following
                    base through a linker moiety (ix) FEATURE:
            (A) NAME/KEY: miscellaneous feature
            (B) LOCATION: 1
            (D) OTHER INFORMATION: thiophosphate group at 5'end
                    of nucleotide strand (xi) SEQUENCE DESCRIPTION: SEQ ID NO:20:

AAAAGTACTA CTCCCTGCTT CTG                             23

(2) INFORMATION FOR SEQ ID NO:21:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO

```
    ( i v ) ANTI-SENSE: NO ( v ) FRAGMENT TYPE:

( v i ) ORIGINAL SOURCE:

( i x ) FEATURE:
            ( A ) NAME/KEY: miscellaneous feature
            ( B ) LOCATION: 1-4
            ( D ) OTHER INFORMATION: A is linked by 2',5'-linkage ( i x ) FEATURE:
            ( A ) NAME/KEY: miscellaneous feature
            ( B ) LOCATION: 4
            ( D ) OTHER INFORMATION: A is linked at 2'end to following
                  base through a linker moiety ( i x ) FEATURE:
            ( A ) NAME/KEY: miscellaneous feature
            ( B ) LOCATION: 23
            ( D ) OTHER INFORMATION: C3 alkylamine moiety linked to 5'end
                  of nucleotide strand ( x i ) SEQUENCE DESCRIPTION: SEQ ID NO:21:

AAAAGTACTA CTCCCTGCTT CTG                                                                    2 3

( 2 ) INFORMATION FOR SEQ ID NO:22:

( i ) SEQUENCE CHARACTERISTICS:
            ( A ) LENGTH: 200 base pairs
            ( B ) TYPE: nucleic acid
            ( C ) STRANDEDNESS: single
            ( D ) TOPOLOGY: linear ( i i ) MOLECULE TYPE: Messenger RNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:22:

AUGGCUGGUG  AUCUUUCAGC  AGGUUUCUUC  AUGGAGGAAC  UUAAUACAUA  CCGUCAGAAG    60

CAGGGAGUAG  UACUUAAAAU  AUCAAGAACU  GCCUAAUUCA  GGACCUCCAC  AUGAUAGGAG    120

GUUUAAUUUC  AAGUUAUAAU  AGAUGGAAGA  GAAUUUCCAG  AAGGUGAAGG  UAGAUCAAAG    180

AAGGAAGCAA  AAAAUGCCCC                                                    200
```

METHOD OF CLEAVING SPECIFIC STRANDS OF RNA AND MEDICAL TREATMENTS THEREBY

The present application is a continuation of application Ser. No. 08/123,449, filed Sep. 17, 1993, now U.S. Pat. No. 5,583,032 which is a continuation-in-part of application Ser. No. 07/965,666, filed Oct. 21, 1992 which is now abandoned. Any disclosure contained in application Ser. No. 07/965,666 which is not included the present application is hereby incorporated by reference.

FIELD OF THE INVENTION

The is invention relates to a method of cleaving specific strands of RNA.

BACKGROUND OF THE INVENTION

Antisense oligonucleotides hold considerable promise both as research tools for inhibiting gene expression and as agents for the treatment of a myriad of human diseases. However, the targeted destruction of RNA using antisense oligonucleotides has been difficult to achieve in a versatile, efficient, and reliable manner.

The potential of oligonucleotides as chemotherapeutic agents has been long appreciated. Levene and Stollar (*Peogr. Allergy,* 12:161 (1968)) found that tetra- and pentanucleotides partially inhibited the binding of nucleic acids to systemic lupus erythematosus sera, while Shen (*Chem. Internat. Ed.,* 9:678 (1970)) suggested the design of high affinity oligonucleotide inhibitors of similar antigen-antibody complexes. Miller, Ts'o, and associates were the first to attempt to capitalize on nucleic acid hybridization through the preparation of a series of trinucleotides modified through phosphotriester, 2'-O-methyl or methylphosphonate substitution (Miller, et al., *Biochemistry,* 13:4887). These short, modified DNA sequences, complementary to t-RNA anticodon regions, were found to be able to inhibit protein translation. Zamecnik and Stephenson (*Proc. Natl. Acad. Sci. U.S.A.,* 74:280 (1978)) used a similar strategy to synthesize a 21 deoxyribonucleotide sequence which inhibited the replication of Rous sarcoma virus.

These early studies were precursors to what is now a burgeoning area of scientific research, i.e. the use of antimessenger/antisense polynucleotides to specifically regulate gene expression. In 1986, additional enthusiasm for this approach was generated by the demonstration that human immunodeficiency virus (HIV) could be inhibited through the use of antisense oligonucleotides (Zamecnik, et al., *Proc. Natl. Acad. Sci. U.S.A.,* 83:7706 (1986)). Although the mechanism of action of such antisense reagents is complex and not well understood, it has been demonstrated that complexes of target messenger RNA and complementary oligo-β-deoxynucleotides are degraded in vivo by the enzyme RNase H, which is present in both eukaryotes and prokaryotes. However, it has been found that many modified antisense oligonucleotides synthesized to improve delivery, cell penetration, or stability will form hybrids with sense strands of RNA but will not act as substrates for RNase H.

Another antisense mechanism which has been found to be operative to some extent is the inhibition of protein synthesis by the passive mechanism of hybridization arrest. By hybridizing an antisense oligonucleotide to a target RNA sequence, the translation of the RNA molecule containing the target sequence can be prevented, thereby inhibiting synthesis of the protein encoded by the RNA molecule. However, because the hybridization of an antisense oligonucleotide to its target ribonucleotide sequence is reversible, this technique cannot totally prevent the translation of the target RNA sequence.

Considerable effort has therefore been directed to the development of oligonucleotides which are able to induce chemical alteration or strand scission of a target RNA molecule. Thus, oligonucleotides have been modified with photoreactive agents such as psoralen or porphyrin (Lee, et al., *Nucleic Acids Res.,* 16:10681 (1988)); oxidative nuclease metal ion complexes such as porphyrin-iron (Doan, et al., *Biochemistry,* 25:6736 (1986)); phenanthroline-copper (Chen, et al., *Proc. Natl. Acad. Sci. USA,* 83:7147 (1986)), and ethylene diamine tetraacetic acid-iron (Dreyer, et al, *Proc. Natl. Acad. Sci. USA,* 82:963 (1985)); nucleases such as staphylococcal nuclease (Corey, et al., *J. Am. Chem. Soc.,* 111:8523 (1989)) and RNase P (Li, et al., *Proc. Natl. Acad. Sci. USA,* 89:3185 (1992)); and catalytic rRNA sequences (Rossi, et al., *Pharmac. Ther.,* 50:245 (1991)). some of these references discuss methods of digesting RNA molecules having a specific nucleotide sequence.

Ying Li et al. (*Proc. of the Natl. Acad. of Sci., U.S.A.,* 89:3185–3189 (1992)), for example, showed that RNase P can be used to cleave specific strands of RNA to which antisense oligonucleotides having an ACCA sequence were annealed. Oligonucleotides with an ACCA sequence at one end, referred to as "external guide sequences" (EGS's), were hybridized to a specific sequence on an RNA molecule. The RNA molecule with the bound EGS thereby became a substrate for RNase P and Was specifically cleaved by RNase P.

Another method of digesting RNA at a specific location with an antisense oligonucleotide and an RNase was demonstrated by Minshull et al. (*Nucleic Acids Research,* 14:6433— 6451 (1986)). Minshull cleaved a specific RNA molecule by first hybridizing an antisense DNA oligonucleotide to the RNA molecule and then treating the hybridized molecule with RNase H. Since RNase H specifically digests DNA/RNA hybrids, the RNA strand of the hybridized molecule was digested by RNase H.

Corey et al. (*J. Am. Chem. Soc.,* 111:8523–8525 (1989)) also discussed a method of targeting a polynucleotide for destruction by a nuclease. Corey fused an antisense oligonucleotide to a nonspecific nuclease. When the oligonucleotide was then hybridized to a polynucleotide with which it could anneal, the nuclease specifically cleaved the targeted polynucleotide strand. This approach has not been applied in vivo, however, due to the great difficulties involved in passing a molecule as large as a nuclease into an intact living cell.

A number of nonenzymatic strategies for targeting a specific polynucleotide sequence for cleavage are also known to the prior art. Many of these involve covalently binding a chemical moiety that has polynucleotide cleavage activity to an antisense oligonucleotide. A method disclosed by Chi-Hong Chen (*Proc. Nat. Acad. Sci. U.S.A.,* 83:7147–7151 (1986)) demonstrated such a strategy. In this method, a 1,10-phenanthroline-copper ion was attached to the 5' end of an oligonucleotide that was complementary to a target polynucleotide sequence. The modified oligonucleotide was hybridized to the complementary target sequence, and cupric ion and 3-mercaptopropionic acid were then added to the reaction mixture. In this environment, the 1,10-phenanthroline-copper ion cleaved the target polynucleotide.

In addition, various non-specific means of cleaving polynucleotides have been identified. For example, the latent endonuclease 2-5A-dependent RNase has been found to cleave RNA in the presence of the unusual 2',5'-phosphodiester-linked trimeric oligoadenylate 2-5A (ppp5'A2'p5'A2'p5'A) (Kerr, et al., *Proc. Natl. Acad. Sci. USA*, 15:9846 (1978)). Cells and tissues examined from reptilian, avian, and mammalian species have been found to contain basal levels of 2-5A-dependent endonuclease, which cleaves RNA after sequences containing UN (where N stands for A, U, G, or C). This enzyme is part of what has been termed the 2-5A system (Williams, et al., *The 2-5A System: Molecular and Clinical Aspects of the Interferon-Related Pathway*, (Alan R. Liss, Inc., New York (1985)), which is believed to mediate certain actions of interferon such as the inhibition of encephalomyocarditis virus replication. The 2-5A system also has been hypothesized to play a role in the regulation of cell growth (Etienne-Smekins, et al., *Proc. Natl. Acad. Sci. USA*, 80:4609 (1983)) and cell differentiation (Krause et al., *Eur. J. Biochem.*, 146:611 (1985)).

SUMMARY OF THE INVENTION

In one aspect, the present invention comprises a method of specifically cleaving a strand of RNA, comprising the steps of:

a. hybridizing the strand of RNA with a chimeric molecule to form a complex of the strand and the chimeric molecule, the chimeric molecule comprising an antisense oligonucleotide moiety that is complementary to the strand of RNA and an activator of 2-5A-dependent RNase attached to the antisense oligonucleotide; and b. reacting the complex in the presence of 2-5A-dependent RNase, thereby specifically cleaving the strand of RNA.

In this method, the chimeric molecule is constructed by first producing an antisense oligonucleotide that is complementary to the strand of RNA to which it will be hybridized, and then attaching this antisense oligonucleotide to an activator of 2-5A-dependent RNase. In this way, a chimeric molecule comprising the antisense oligonucleotide and the activator is produced. The activator used in this method can comprise a 2',5'-oligonucleotide, such as 2-5A, but may be any activator of 2-5A-dependent RNase. The 2-5A can itself be p5'A2'p5'A2'p5'A. Preferably, the strand of RNA to which the chimeric molecule hybridizes is mRNA that is located in a cell.

In another aspect of the present invention, a method of specifically cleaving a strand of RNA contained in a cell is disclosed. This methods comprises the steps of:

a. contacting the cell with a chimeric molecule, the chimeric molecule comprising an antisense moiety and an activator of 2-5A-dependent RNase attached to the antisense moiety, the antisense moiety being capable of binding or annealing to the strand of RNA contained in the cell;

b. passing the chimeric molecule into the cell; and thereafter c. reacting the chimeric molecule with the strand of RNA in the presence of 2-5A-dependent RNase, thereby causing the strand of RNA to become cleaved.

In this method, the activator can be a molecule of 2-5A, such as p5'A2'p5'A2'p5'A. The antisense moiety can also be an antisense oligonucleotide. Preferably, the chimeric molecule used in this method is contacted with the cell at a concentration of between 0.1 µM and 100 µM, and more preferably at a concentration of between about 1.0 µM and 5.0 µM. This method can also additionally comprise the step of identifying an antisense moiety which can bind or anneal to a single stranded region of the strand of RNA contained in the cell. This strand of RNA can be, for example, the RNA transcript of an oncogene or a proto-oncogene, the RNA transcript of a viral protein, or the genome of an RNA virus.

In yet a further aspect, the present invention comprises a method of treating a medical condition in a subject whose cells contain the enzyme 2-5A-dependent RNase, wherein a strand of RNA contained in at least some of the cells of the subject is involved in producing the medical condition. Since the cells of mammals (including humans), birds, and reptiles have all been found to contain 2-5A-dependent RNase, the subjects of this method can be chosen from any of these groups, or from any other group of subjects whose cells contain 2-5A-dependent RNase. The method comprises the step of administering a chimeric molecule in a pharmacologically acceptable carrier to the subject in an amount which is effective to treat the medical condition.

The chimeric molecule used in the foregoing method contains an antisense moiety, preferably an antisense oligonucleotide, that is capable of binding or annealing to the strand of RNA. The chimeric molecule also comprises an activator of 2-5A-dependent RNase. The activator used in this method is preferably a 2'-5'-oligonucleotide, such as 2-5A or p5'A2'p5'A2'p5'A, but can be any activator of 2-5A-dependent RNase. This method can also comprise the additional step of identifying a single stranded region of the strand of RNA contained in the cell to which the antisense moiety can bind or anneal. The strand of RNA involved in producing the medical condition can be, for example, mRNA. The strand of RNA can also be the RNA transcript of an oncogene or a proto-oncogene the RNA transcript of a viral protein, or the genome of an RNA virus. In this method, the chimeric molecule can be administered intravenously, topically, or by direct infusion into a desired tissue. Preferably, the subject of this method is a human being.

Yet another aspect of the present invention is a chimeric molecule comprising an antisense moiety attached to an activator of 2-5A-dependent RNase. The antisense moiety can be, for example, a 3',5'-oligonucleotide which is preferably a deoxyoligonucleotide. The activator preferably comprises 2-5A, though other activators can of course also be used. This chimeric molecule can be modified to comprise a 5'-thiophosphate group or to include a 3'-tail moiety, such as an alkyl amine group. The chimeric molecule can also comprises both a 5'-thiophosphate group and a 3'-tail moiety.

DETAILED DESCRIPTION OF THE INVENTION

I. Definitions

"Antisense"

Figure 1:
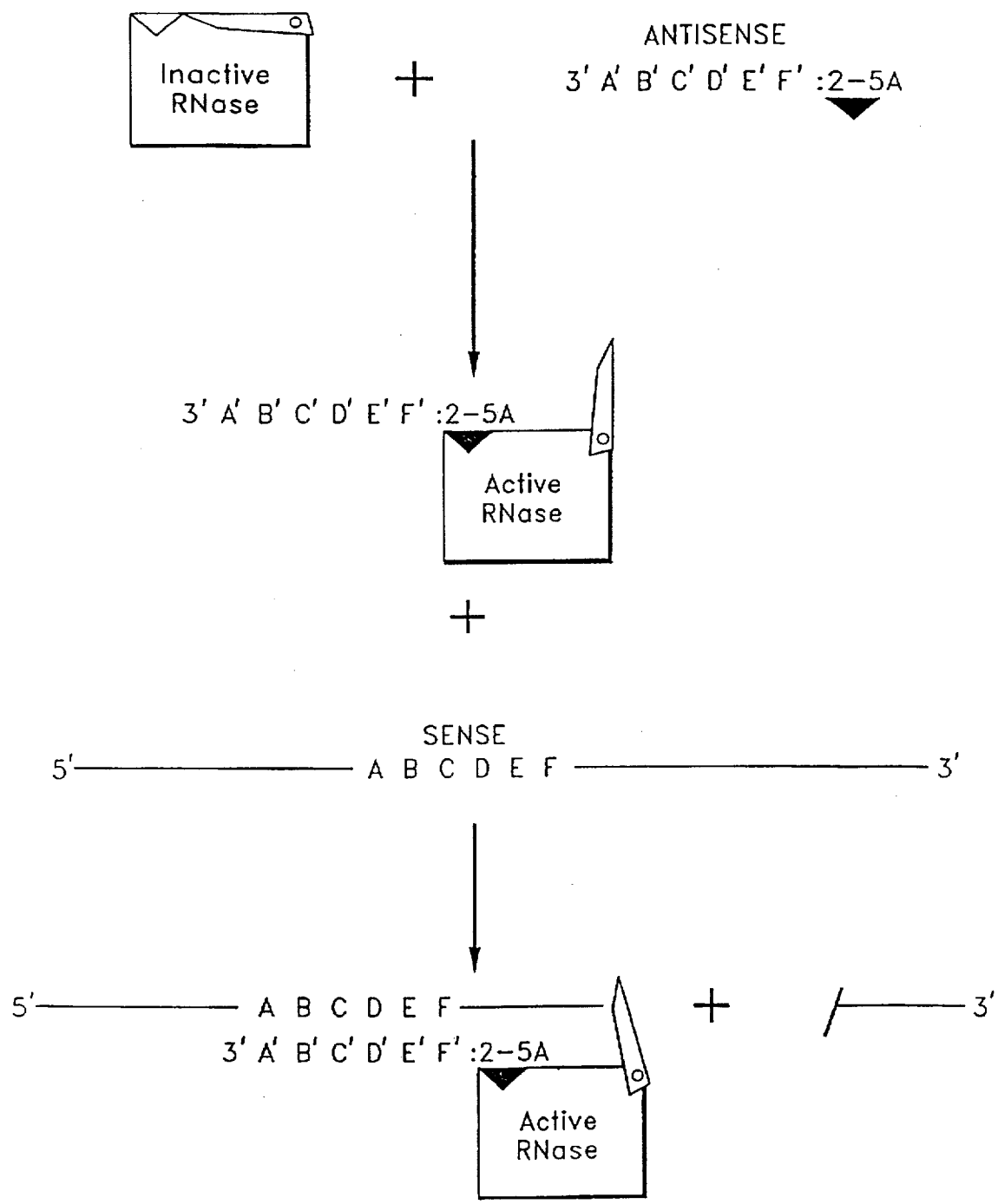
FIG. 1 is a schematic representation of a method of targeting a molecule of RNA containing a specific sequence for cleavage by using an antisense oligonucleotide coupled to a 2-5A molecule.

An antisense moiety is a molecule, often comprising an oligonucleotide and preferably composed of DNA, which is complementary to or capable of binding to a strand of RNA which is targeted for cleavage according to the present methods. This targeted strand of RNA can be referred to as a sense strand of RNA or as a target RNA molecule.

When an antisense moiety is an oligonucleotide, this oligonucleotide can be referred to as an antisense oligonucleotide. The antisense oligonucleotides described below are most frequently 3',5'-linked oligodeoxynucleotides. It is also possible, however, for molecules besides 3',5'-linked oligodeoxynucleotides to serve as antisense moieties. For example, a molecule composed of bases that are linked together without sugar moieties which can bind to a specific sequence in a strand of RNA can be used as an antisense moiety according to the present invention. The following are examples of possible antisense moiety constituents: 2'-O-methyloligoribonucleotides; oligodeoxyribonucleotide phosphorothioates; alpha-deoxynucleotides; carbamate-linked oligonucleotide analogs; methylphosphonate oligonucleotide analogs; nucleobases appended to a backbone of acryloylnucleoside-acrylamide (see Zon, G., *Pharmaceutical Research*, 5:539–549 (1988)); and vinyl backbone-based nucleic acid analogs (see Pitha, P. M. and Pitha, J., *Biopolymers*, 9:965–978 (1970)).

Proteins and other factors Which bind to a specific region of RNA can also be used as antisense moieties. The tat protein, a peptide which binds to the TAR region of HIV RNA, can, for example, be used as an antisense moiety for binding to and cleaving such HIV RNA. An RNA virus transactivation factor can also be linked to an RNase activator moiety such as 2-5A in order to effect the destruction of viral RNA. In addition, a transcription factor can be used as an antisense moiety in order to target nascent RNA as it is generated from genomic DNA. Therefore, although antisense oligonucleotides are used in most of the specific examples of the present invention described below, such examples should not be construed so as to exclude other types of antisense moieties from the scope of the present invention.

"RNase Activator"

An RNase activator is a molecule which is capable of activating an RNase so that it will cleave RNA. For example, the molecule 2-5A is an RNase activator which activates 2-5A-dependent RNase to cleave RNA. As used herein, the term 2-5A encompasses oligoadenylate molecules made up of adenosines that are linked at their 2' and 5' carbons through phosphodiester bonds to other adenosine molecules. However, it is to be understood that other oligonucleotides or molecules capable of activating 2-5A-dependent RNase can also be used in place of 2-5A in the chimeric molecules of the present invention. Thus, the term 2-5A as used herein encompasses such other oligonucleotides and molecules.

When describing 2-5A and other molecules, the notation "p5'A2'" is used to denote an adenosine molecule ("A") linked to another molecule, typically another nucleotide, via a phosphodiester bond at the 2' and 5' hydroxyl groups of the adenosine molecule. The "p" preceding the 5' notation is shorthand for a phosphate group. The leftmost adenosine is at the 5' end of the oligoadenylate molecule, and if that molecule is preceded by a "p", this indicates that hydroxyl group of the indicated carbon is phosphorylated. One "p" denotes monophosphorylation, while "pp" denotes diphosphorylation, etc. Thus, the notation p5'A2'p5'A2'p5'A2'p5'A denotes an oligoadenylate molecule composed of 4 adenosines linked through the hydroxyl groups of the 2' and 5' carbons by phosphodiester bonds, with the 5' end of the oligoadenylate molecule carrying a monophosphate moiety on the hydroxyl group of the 5' carbon of the 5' adenosine molecule.

"Chimeric Molecule"

A chimeric molecule, as that term is used herein, is a molecule comprising an RNase activator joined to an antisense moiety, such as a 3',5'-antisense oligonucleotide. In order to join an RNase activator to an antisense moiety, linker molecules can be used but are not absolutely required. Chimeric molecules comprised of 2-5A and an antisense moiety will be denoted herein as 2-5A:AS.

"Complementary"

A nucleotide strand is said to be complementary to another nucleotide strand if the two strands can anneal under reaction conditions which allow the chimeric molecule of the present invention to induce the cleavage of a sense strand of RNA. Exact complementarity (where each molecule of adenine of a nucleotide strand binds to a molecule of thymine or uracil on another strand and each molecule of guanine binds to a molecule of cytosine) is encompassed by this term. However, a chimeric molecule which contains an antisense moiety having a limited number of mismatches or intervening sequences which disrupt the exact complementarity of its sequence with the sequence of a target RNA molecule can also be a complementary molecule. In order for such a chimeric molecule to be complementary, it must be capable of annealing to the target RNA molecule under reaction conditions which allow the specific cleavage of the target RNA molecule by an RNase activated by the chimeric molecule, such as 2-5A-dependent RNase, according to the present methods.

Using the parameters provided herein and information known to the prior art, such as the relative strength of GC bonding, one of ordinary skill of the art can determine whether two molecules are sufficiently complementary to be used in the present invention. For example, a 2-5A-containing chimeric molecule comprising a 19 nucleotide-long antisense oligonucleotide moiety which contains 10 mismatches compared to a target RNA molecule has been found to be unable to cause the cleavage of the target RNA molecule. Therefore, this chimeric molecule is not complementary to such a target RNA molecule. The determination of the complementarity of a particular chimeric molecule with a particular target RNA molecule, however, is a matter within the ability of one of skill in the art as well as being a matter of routine experimentation.

"Hybridize"

Hybridization is the process of annealing nucleic acid molecules. Typically, this involves annealing single stranded molecules in order to form a duplex strand of nucleic acids. Such a duplex strand would comprise two single stranded molecules bonded to each other through hydrogen bonds. Higher order hybridizations, however, are also possible. For example, a single stranded nucleic acid molecule can be hybridized to a double stranded nucleic acid molecule to form a triple helix.

Hybridization occurs spontaneously under conditions known to those of skill in the art. For example, the conditions stated in Sambrook, Fritsch, and Maniatis, *Molecular Cloning: A Laboratory Manual*, Second Edition, Cold Spring Harbor (1989) can be used to induce the hybridization of nucleic acid sequences. The conditions present within a living mammalian cell are particularly preferred. The hybridization conditions used in the methods of the present invention should support both the hybridization of nucleic acids and the cleavage of RNA by an activated RNase. Thus, when the chimeric molecule used in the present methods is a molecule of 2-5A:AS whose antisense moiety is an antisense oligonucleotide, hybridization conditions which also allow activated 2-5A-dependent RNase to cleave RNA are preferred.

"React"

A chimeric molecule can be said to react with a sense strand of RNA when put into contact with that strand in the presence of an RNase. This reaction causes the cleavage of the sense strand. It is believed that the cleavage reaction occurs either during or after the hybridization or binding of the chimeric molecule with the sense strand of RNA, and that the cleavage is effected by an activated RNase. In the preferred embodiment of the present invention, the RNase is 2-5A-dependent RNase, which is activated by a 2-5A moiety of the chimeric molecule. However, it is possible that the chimeric molecule used in the present methods produces the cleavage of a sense strand of RNA in some other way in addition to or instead of through the mechanism of action hypothesized herein as being the mechanism by which the chimeric molecule acts. Therefore, the term "react" when used to describe the interaction of a chimeric molecule and a sense strand of RNA is to be interpreted broadly and is not to be limited to the mechanism of action proposed herein.

The foregoing terms, including plurals, gerunds, and other grammatical permutations thereof, shall be given the definitions provided above unless otherwise stated herein or unless a different meaning is clearly indicated in context.

Other terms and phrases are also defined herein as necessary in order to clarify the meaning of Such terms and phrases.

II. Cleaving RNA Strands with a Unique Chimera

We have developed a novel and effective strategy for cleaving specific RNA sequences which makes use of an RNase activator molecule that is covalently linked to an antisense moiety, such as an antisense oligonucleotide. In the preferred embodiment of the present invention, the RNase activator is a molecule of 2-5A, such as p5'A2'p5'A2'p5'A2'p5'A. In this strategy, a chimeric molecule such as 2-5A:AS is contacted with an RNA molecule with which the antisense moiety of the chimeric molecule can anneal or bind. For example, an antisense oligonucleotide moiety of a molecule of 2-5A:AS can be contacted with a strand of RNA with which it is complementary (i.e., a sense strand of RNA). In this preferred embodiment, it is believed that the 2-5A component of the chimeric molecule activates a molecule of 2-5A-dependent RNase and that the antisense portion of the 2-5A:AS molecule directs the specific cleavage of the sense strand RNA molecule by 2-5A-dependent RNase. This strategy and its theorized mechanism of action are shown schematically in FIG. 1.

The RNase used in the preferred embodiment of the present invention is 2-5A-dependent RNase (also called RNase L), an endoribonuclease which has been shown to be involved in mediating the inhibitory effects of interferon on viral infection. This RNase is found ubiquitously in mammalian cells. 2-5A-dependent RNase is normally inactive unless activated by 5'-phosphorylated 2',5'-linked oligoadenylates known as 2-5A, $[p_n5'A2'(p5'A2')_np5'A]$. The activation of 2-5A-dependent RNase causes this enzyme to cleave single-stranded RNA, predominantly after UU and UA sequences.

While a 5'-triphosphate group is required to activate some forms of 2-5A-dependent RNase, we and others have found that the human 2-5A-dependent RNase requires only a 5'-monophosphorylated 2',5'-oligoadenylate to be effectively activated. Other 2',5'-oligonucleotide analogs have also been shown to be effective in activating 2-5A-dependent RNase. See, e.g., Williams et al., *The 2-5A System: Molecular and Clinical Aspects of the Interferon-Regulated Pathway*, pp. 75–80 (1985); Torrence, et al., *Chemica Scripta*, 26:191–197 (1986); Kitade, et al., *Bio-organic Chemistry*, 19:283–289 (1991); and Kitade, et al., *Nucl. Acids Res.*, 19:4103–4108 (1991). Therefore, although the present invention is described in terms of antisense moieties joined to 2-5A, the term 2-5A is meant to include other 2',5'-oligonucleotide analogs which are able to activate 2-5A-dependent RNase.

To direct 2-5A-dependent RNase to cleave unique RNA sequences, 2-5A is attached to an antisense moiety, such as an antisense oligonucleotide which is complementary to a target RNA molecule. Any antisense oligonucleotide molecule that is complementary to a target RNA molecule that is desired to be cleaved can be chosen as the antisense oligonucleotide moiety of a molecule of 2-5A:AS, as long as that antisense oligonucleotide moiety will be able to hybridize to the target RNA molecule under the reaction conditions used.

Although target RNA molecules are generally single stranded, a single stranded RNA molecule will sometimes form intramolecular hydrogen bonds, depending on the nucleotide sequence of the RNA molecule and the conditions to which it is exposed. Such bonding is referred to as secondary structure, and such secondary structure can sometimes, though not necessarily always, interfere with the hybridizing of an antisense oligonucleotide moiety to a target RNA molecule which has secondary structure. Therefore, an antisense oligonucleotide moiety for a chimeric molecule is preferably selected so as to be complementary to a portion of a target RNA molecule which does not bond intramolecularly in order to avoid any potential interference with hybridization due to target RNA secondary structure. An example of a relatively unhindered portion of an RNA molecule which is preferably selected for cleavage is the region of 19 nucleotides located between the arrows labeled 10 and 11 in FIG. 8.

In order to select an antisense oligonucleotide moiety which avoids such secondary structure, one of skill in the art can use a computer program which predicts the secondary structure of a particular RNA molecule in order to first determine which portions of the target RNA molecule are subject to such secondary structure. Target RNA sequences which are not likely to form intramolecular hydrogen bonds (and are therefore single stranded), which are of appropriate length to allow antisense oligonucleotide hybridization, and which are not otherwise sterically hindered by secondary structure are preferred target sequences for cleavage by a chimeric molecule. In order to select such target RNA sequences, a computer program such as MULFOLD version 2.0 (the Macintosh version of MFOLD) according to Michael Zuker and John Jaeger can be used. MULFOLD is a public domain program which predicts RNA secondary structure by free energy minimization, including suboptimal folding with temperature dependence (provided by Don Gilbert, Biocomputing Office, Biology Department, Indiana University, Bloomington, Ind.). Secondary structure can also be predicted without a computer program by one of skill in the art through reference to publications such as Zuker, M., "On Finding All Suboptimal Foldings of an RNA Molecule, *Science*, 244:48–52 (1989) and Jaeger, J. A. et al., "Improved Predictions of Secondary Structures for RNA," *Proc. Natl. Acad. Sci. USA*, 86:7706–7710 (1989).

In the methods of the present invention, a 2-5A:AS molecule which is selected and produced as described herein is contacted with a target RNA molecule under conditions which allow the 2-5A:AS molecule to hybridize or otherwise bind to the target RNA molecule. It is believed that the interaction of the 2-5A:AS molecule with the target RNA molecule, combined with the interaction of the 2-5A:AS molecule with 2-5A-dependent RNase, together act to cause the specific cleavage of the target RNA molecule. Under conditions, such as in a reaction medium containing 100 nM target RNA, 150 nM 2-5A:AS, and 2-5A-dependent RNase (100 ng per microtiter assay, in a total volume of about 20 μl) at 37° C. and physiological pH, almost complete cleavage of the target RNA molecules can occur in under five minutes.

By cleaving a molecule of RNA having a particular sequence, if the molecule is a molecule of mRNA, then the expression of the protein for which that RNA molecule coded can be inhibited. This is due to the fact that a full transcript RNA molecule will not be available for translation once that RNA molecule has been cleaved. Thus, a complete form of the protein will not be produced, and the expression of that protein will be inhibited. Preferably, the antisense portion of the 2-5A:AS chimera is therefore selected so as to be complementary to a portion of the target RNA molecule near the start codon of the target mRNA molecule and slightly downstream (toward the 3' end of the molecule) of that start codon. In this way, the chances of preventing the translation of the active or functional portion of the protein for which the target RNA codes are maximized.

A. Synthesis and Characterization of 2-5A:AS Molecules

The synthesis of 2-5A:AS chimeric molecules which can be used in the methods of the present invention involves the covalent coupling of a 2-5A molecule to an antisense moiety such as a 3',5'-linked antisense oligonucleotide. As previously stated, the 2-5A moiety of this chimeric molecule can comprise any of a number of 2',5'-oligoadenylate analogs. The antisense oligonucleotide moiety of the 2-5A:AS molecule can also comprise any oligonucleotide which is complementary to a target RNA molecule which is desired to be cleaved. Preferably, the antisense oligonucleotide moiety of the 2-5A:AS molecule used in the methods of the present invention is perfectly complementary to a target sequence of RNA. The 2-5A and antisense oligonucleotide components of a 2-5A:AS chimeric molecule can be produced by any means known to those of skill in the art. These components can be produced, for example, with a DNA synthesizer.

The 5'-terminus of the antisense oligonucleotide moiety of a molecule of 2-5A:AS is preferably linked to the 2'-terminus of the 2',5'-oligoadenylate. Other linkage modes are also possible, however. Linkages between the antisense oligonucleotide moiety and the 2-5A moiety through the 5'-terminus of the 2-5A moiety, though, are-not recommended because it is known that the incorporation of the 5'-phosphate into an internucleotide is likely to result in diminished binding of the 2-5A moiety to 2-5A-dependent RNase (Torrence, et al., *Med. Chem.*, 27:726 (1984)). The antisense oligonucleotide and 2-5A moieties of the chimeric molecule can be attached to one another by any method known to the art. For example, hexane diol or ethane diol can be used as a linker molecule. The antisense and 2-5A moieties can also be attached to one another directly without the use of a linker molecule.

The following semi-automated procedure can be used to synthesize 2-5A:AS chimeric molecules. With this procedure, chimeric molecules having the general formula: p5'A2'p5'A2'p5'A2'p5'A2'p($CH_2$)$_4$p($CH_2$)$_4$p5'-(antisense oligonucleotide) can be produced.

I. Reagents and Chemicals Employed

In this semi-automated procedure, all solid chemicals are first preferably dried over $P_2O_5$ in vacuo before use. For the initiation of synthesis on a solid support, about 1 μmole of the following reagents are used:

5'-O-dimethoxytrityl-$N^4$-benzoyl-2'-deoxycytidine-CPG
5'-O-dimethoxytritylthymidine-CPG
5'-O-dimethoxytrityl-$N^2$-isobutyryl-2'-deoxyguanosine-CPG
5'-O-dimethoxytrityl-$N^6$-benzoyl-2'-deoxyadenosine-CPG These DMT protected nucleosides are all attached to controlled pore glass (CPG) through a succinyl group and a long chain alkyl amine linker and can be obtained as commercial products of Applied Biosystems (Foster City, Calif.).

For the synthesis of the 2',5'-oligoadenylate domain of the chimera, 0.1M of the following compound in dry acetonitrile is used:

5'-O-dimethoxytrityl-$N^6$-benzoyl-3'-O-t-butyldimethylsilyladenosine-2'-N,N-diisopropyl-cyanoethylphosphoramidite (Chemgenes Corporation, Waltham, Mass., cat. no. ANP 5681).

For the elongation of the DNA antisense chain, a total of 500 mg of each of the following phosphoramidites (obtained from Applied Biosystems) is dissolved in the amount of anhydrous acetonitrile indicated in parentheses:

$N^4$-benzoyl-5'-O-dimethoxytrityl-2'-deoxycytidine-3'-N,N-diisopropyl-cyanoethylphosphoramidite (5.9 mL);

N²-isobutyryl-5'-O-dimethoxytrityl-2'-deoxyguanosine-3'-N,N-diisopropyl-cyanoethylphosphoramidite (5.8 mL);
5'-O-dimethoxytrityl-2'-deoxythymidine-3'-N,N-diisopropyl-cyanoethylphosphoramidite (6.6 mL); and
N6-benzoyl-5'-O-dimethoxytrityl-2'-deoxyadenosine-3'-N,N-disopropyl-cyanoethylphosphoramidite (5.6 mL).

The following linker can be used to join the 2-5A and antisense chimeric domains:
(2-cyanoethyl-N,N-diisopropyl)[4-O-(4,4'-dimethoxytrityl)-butyl]phosphoramidite.

This linker is used at a concentration of 0.2M in tetrazole/acetonitrile (Applied Biosystems).

The phosphorylation reagent which is used in this procedure at the 5'-terminus of the 2',5-oligoadenylate domain of the chimeric molecule is: 2-[2-(4,4'-Dimethoxytrityloxy)ethylsulfonyl]ethyl-2-cyanoethyl)-(N,N-diisopropyl)-phosphoramidite (obtained from Glen Research, Sterling, Va.; catalog no. 10-1900-90). This reagent is present in anhydrous tetrazole/acetonitrile (obtained from Applied Biosystems) at a concentration of 0.2M.

Other reagents employed in the synthesis of the DNA antisense region of the 2-5A:AS constructs are standard reagents available commercially for use in automated DNA synthesis and are supplied by Applied Biosystems. These reagents include Diluent (acetonitrile), Activator Solution (tetrazole solution), Capping Solution A (acetic anhydride solution), Capping Solution B (N-nethylinidazole solution), Deblock Solution (dichloroacetic acid solution), and Oxidizer (iodine solution).

Tetrabutylammonium fluoride in tetrahydrofuran (1M solution) is used to deblock the t-butyldimethylsilyl groups used to protect the 3'-hydroxyls of the 2',5'-oligoriboadenylate domain.

2. Synthetic Procedure

The antisense region of a chimeric molecule is synthesized in this procedure using a DNA synthesizer, such as an Applied Biosystems model 391 DNA synthesizer, and the aforementioned reagents and solvents. After inputting the sequence of the desired antisense oligonucleotide to be produced into the microprocessor of an Applied Biosystems model 391 DNA synthesizer, cycle 2 is selected for the 1 μmole scale, and the trityl off mode is activated. Once the synthesis of the antisense oligonucleotide is complete, the column is dried by flushing with anhydrous argon for 60 seconds. Next, the linker is coupled to the protected antisense oligonucleotide. The coupling cycle employed is summarized in Table 1 below.

TABLE 1

| STEP | SOLVENTS/REAGENTS | TIME | VOLUME |
|---|---|---|---|
| Detritylation | 2% TCA in CH₂Cl₂ | 90 s | 1 mL |
| Washing | 1% pyridine in CH₂CN | | 1 mL |
| Washing | CH₃CN | | 4 mL |
| Dry | nitrogen | 3 min | |
| Coupling | 0.1M linker in CH₃CN/tetrazole | 5 min | .15 mL |
| Washing | CH₃CN | | 4 mL |
| Dry | nitrogen | 3 min | |
| Capping | Capping solution A & B | 2 min | .9 mL |
| Washing | CH₃CN | | 4 mL |
| Dry | nitrogen | 3 min | |
| Oxidation | 0.1M I₂ lutidine/THF/H₂O (20:80:1) | 45 s | 1 mL |
| Washing | CH₃CN | | 4 mL |
| Dry | nitrogen | 3 min | |

The cycle outlined in Table 1 above is repeated twice if two linker molecules are to be added to the antisense oligonucleotide, since a complete cycle is required for the addition of each of the two butanediol linkers to the oligonucleotide. The DMT group is not removed at the end of the second cycle. The oligonucleotide product of the above series of manipulations is transferred, while still attached to the CPG support, to the DNA synthesizer for addition and elongation of the 2',5'-oligoadenylate terminus of the chimeric molecule.

For the final automated step of this synthesis, 5'-O-dimethoxytrityl-N⁶-benzoyl-3'-O-t-butyldimethylsilyladenosine-2'-N,N-diisopropyl-cyanoethylphosphoramidite is employed as the only nucleotide addition reagent. On the Applied Biosystems DNA synthesizer, the coupling wait time is increased to 600 s, the mode is trityl off, and cycle 3 is activated. The microprocessor input sequence is, for this 5'-terminal addition of 2',5'-oligoadenylate tetramer, XXXX G, where G stands for the linker-antisense oligomer-CPG and XXXX stands for the 2'5'-adenosine moieties which are to be added.

The 5'-phosphorylation of the 2-5A moiety which created through the foregoing synthesis is accomplished manually with the column removed from the synthesizer. The reagent used is: 2-[2-(4,4'-dimethoxy-trityloxy)ethylsulfonyl]ethyl-2-cyano-ethyl)-(N,N-diisopropyl)-phosphoramidite (Glen Research, Sterling, Va.; catalog no. 10-1900-90). This reagent is used at a concentration of 0.2M in anhydrous tetrazole/acetonitrile (Applied Biosystems). The coupling time is 3 min. Oxidation with iodine solution is for 45 seconds. Finally, the product is detritylated and dried.

3. Cleavage and Deprotection

The oligonucleotide is cleaved from the support by concentrated NH₄OH/ethanol (3:1, v/v) treatment at room temperature for 2 hours. The inclusion of the ethanol in this deprotection step is necessary to solubilize adequately the more lipophilic 2'-O-silyl oligoribonucleotide and to minimize desilylation.

The ammonia/ethanol solution of crude oligonucleotide is next removed into a 3 mL vial which is sealed tightly. This is heated at 55° C. for 8 hours to remove the protecting groups of the bases.

The resulting NH₄OH/ethanol of oligonucleotide is then transferred to a glass tube and cooled in an ice-bath. The solution then is reduced to dryness in vacuo in a SPEED-VAC™ apparatus (Savant Instruments Inc., Farmingdale, N.Y.), and a solution (1 mL of 1M) of tetrabutylammonium fluoride in dry tetrahydrofuran is added, and the entire mixture is vortexed at room temperature for at least 1 minute. This reaction mixture is then allowed to incubate at room temperature for 10 hours.

Following this, an equivalent volume of an aqueous triethylammonium acetate (TEAA) solution (0.1M) is added, and after mixing, the entire solution is evaporated to near dryness. TEAA (0.1M, 1 mL) again is added, and the entire solution is applied to a C-18 SEP-PAK cartridge (Supplied by Waters Associates) in order to remove unwanted reagents, after the cartridge had been pre-washed with 10 mL methanol followed by 10 mL of H₂O. The loaded cartridge is washed consecutively with: 1) 15 mL H₂O; 2) 10 mL 5% MeOH in H₂O; and finally 3) 10 mL 10% MeOH in H₂O. The cartridge then is eluted with 10 mL 50% MeOH in H₂O. Oligonucleotide-containing fractions are determined using UV spectrophotometry, and appropriate fractions are combined and concentrated on the SPEED-VAC™ apparatus.

4. Oligonucleotide Purification

The chimeric oligonucleotide is purified by HPLC under the following conditions:

A Nucleogen DEAE 60-7 ion exchange column (4×125 mm, Rainen Instrument Co. cat no. 718596; solvent A, 20 mM potassium phosphate (pH 7.0) in 20% CH₃CN; solvent B, 20 mM potassium phosphate (pH 7.0) in 1M KCl) is used. The program for elution is: 10–80% solvent B in solvent A over 30 minutes and then 80% solvent B in solvent A for 10 minutes (flow rate=1 mL/min).

After the above purification, the product is desalted and concentrated on a C-18 SEP-PAK cartridge using the following protocol:

a. The C-18 SEP-PAK column is pre-washed with 10 mL MeOH followed by 10 mL H₂O;

b. The oligonucleotide solution is loaded onto the cartridge in a total volume of 2–5 mL;

c. The cartridge is washed with 20 mL H₂O and then with 10 mL of 5% MeOH in H₂O;

d. The oligonucleotide product is eluted with 10 mL of 50% MeOH. Fractions are collected, checked with UV spectrophotometry, and appropriate fractions are combined and concentrated to dryness on a SPEED-VAC™ apparatus.

5. Nucleotide Composition Analysis

The chimeric molecules produced through the above protocol are next preferably analyzed for their nucleotide composition by enzymatic digestion with snake venom phosphodiesterase (Pharmacia Inc., Piscataway, N.J., cat no. 27,0821-01). The enzyme-catalyzed hydrolysis conditions are: 0.2 A₂₆₀ unit of chimeric molecule, 0.15 units of snake venom phosphodiesterase, in a final volume of 100 μL which is 50 mM in Tris-HCl (pH 8.0) and 0.5 mM in MgCl₂. Incubation is at 37° C. for 3 hours.

The digested sample is then analyzed by HPLC by injecting 10 μL onto a Ultrasphere ODS column (0.46×25 cm). Separation of the digestion products is accomplished with the following elution program: 2% solvent B in solvent A over 20 min and then 2–55% B in A over 15 min (flow rate of 0.5 mL/min) where solvent A is 100 mM ammonium phosphate (pH 5.5) and solvent B is MeOH/H₂O (1:1). The approximate retention times of the products of digestion are: dCMP, 9 minutes; dTMP, 22 minutes; dGMP, 24 minutes; AMP, 26 minutes; pA$_{linker}$ (where the linker is composed of two molecules of butane diol), 33 minutes; dAMP, 35 minutes. The molar ratios of digestion products are determined by integration of the recorded UV absorption at 260 nm.

6. Purity Confirmation

Each product is checked for purity by HPLC and by high performance capillary electrophoresis which is carried out on an Applied Biosystems 270A-HT capillary electrophoresis instrument using MICRO-GEL₁₀₀™ (Applied Biosystems) gel-filled capillaries (50 μm i.d., effective length 27 cm; running buffer, 75 mM Tris phosphate (pH 7.6)/10% MeOH. Detection is carried out at 260 nm.

The following Examples provide specific examples of the synthesis and characterization of 2-5A:AS chimeric molecules which can be used in the methods of the present invention.

EXAMPLE 1

Synthesis of Experimental 2-5A:AS Chimeras

For prototype synthetic and in vitro evaluation experiments, chimeric molecules were prepared, including an oligo dT 18-mer comprising the tetrameric 2'5'-phosphodiester-linked oligoadenylate p5'A2'p5'A2'p5'A2'p5'A. The following chimeric molecules comprising oligo-dT moieties and 2',5'-phosphodiester-linked oligoadenylate molecules were prepared according to the protocol below:

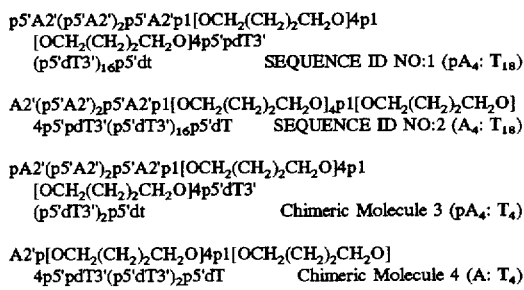

Producing these oligonucleotides was performed manually on DNA synthesis columns (1.5 cm, American Bionetics, Inc.) loaded with approximately 1.5 μmole of CPG-bound 5'-O-dimethoxytritylthymidine (Pond et al., Biotechniques, 6:768 (1988)), using adapters and gas-tight syringes (Uznanski, et al., Chem. Scripta, 26:221 (1986)). Syntheses were controlled by quantitating spectrophotometrically the release of the dimethoxytrityl cation. The synthesized oligonucleotides were cleaved from the support with concentrated ammonia/ethanol (3:1) by a 2 hour incubation at room temperature. N⁶-Benzoyl groups were removed by warming the resulting ethanolic solutions for 6 hours at 55° C. Finally, the 3'-O-t-butyldimethylsilyl protecting groups were removed by treatment with 1M tetrabutylammonium fluoride in THF for at least 12 hours at room temperature.

The linker was prepared for attaching the antisense oligonucleotides to the 2-5A. The linker used was produced from a protected intermediate, 4-O-(4,4'-dimethoxytrityl)-1,4-butanediol. To prepare this protected linker, 1,4-butanediol (10 mmole) was dried by repeated coevaporation with anhydrous pyridine and then dissolved in 50 ml of the same solvent. To this solution 4,4'-dimethoxytrityl chloride (3390 mg, 10 m mole) was added and the mixture was kept for 2 hours at room temperature.

The reaction was terminated by pouring the mixture into a beaker containing ice (100 g) and the desired products were extracted with ethyl acetate. The extract was dried with magnesium sulfate, concentrated, and purified on a silica gel column which then was eluted with methylene chloride containing 1% methanol. The yield, as measured by NMR, was as follows: 870 mg (22%): ¹H-NMR(CDCl₃, 1% deuteriopyridine), δ(ppm): 1.68 (m, 4H, CH₂); 3.10 (t,J=5.7 Hz, 2H, CH₂—O); 3.62(t,J=5.8 Hz, 2H, CH₂—OH); 3.76(s, 6H,CH₃—O); 6.79–7.46 (m, aromatic). High resolution mass spectrum (electron impact) analysis was as follows: calculated for C₂₅H₂₈O₄ 392.1988, found 392.1981. This product was then converted to (2-cyanoethyl)-(N,N-diisopropyl)[4-O-(4,4'-dimethoxybutyl)]phosphoramidite for use as linker in the chain extension to add the 2-5A moiety to the oligonucleotide component.

A solution of 2-cyanoethyl-N,N-diisopropylchlorophosphoramidite (237 mg, 1 mmol) was added slowly under anhydrous conditions with cooling (ice bath) to a solution of 4-O-(4,4'-dimethoxytrityl)-1,4-butanediol (390 mg, 1 mmol) and N-ethyldiisopropylamine (510 mg, 4 mmol) in anhydrous methylene chloride (3 ml). This mixture was kept at room temperature for 1 hour, after which the solvent was evaporated and the product purified on a silica gel column (1.8×14 cm, eluted with benzene-petroleum ether-triethylamine, 6:3:1). As measured by NMR, the yield was: 530 mg (90%): ¹H-NMR(CDCl₃, 1% deuteriopyridine) δ(ppm): 1.17 (t, J=7.0 Hz, 12H, CH₃—C); 1.70 (m, 4H, CH₂—C); 2.60 (t, J=6.5 Hz, 2H, CH₂—CN);

3.08 (t, J—5.7 Hz, 2H, CH$_2$—O); 3.80 (m, 4H, CH$_2$—O—P); 3.78 (s, 6H, CH$_3$—O); 3.80 (m, 2H, CH), 6.80–7.49 (m, aromatic); $^{31}$P NMR (CDCl$_3$, 1% deuteriopyridine) δ(ppm): 147.6. High resolution mass spectrum (FAB) analysis was as follows: calculated for C$_{34}$H$_{46}$N$_2$O$_5$P 593.3144, found 593.3112.

Chimeric Molecule 3 was purified using an HPLC (High Performance Liquid Chromatography) device consisting of two Beckman 110 B solvent delivery modules (Beckman Instruments Inc., Fullerton, Calif.) controlled by an NEC computer, a Beckman 153 UV detector for detecting at 254 nm, and a semipreparative Ultrasphere ODS column (flow rate 2 ml/min, linear gradient of 20–100% buffer B in buffer A for 30 min, where buffer A was 50 mM ammonium acetate (pH 7.0) and buffer B was 50% methanol/water). SEQ ID NO:1 was purified on a Vydac column using the above HPLC system and a flow rate of 1 ml/min with a elution program of 0.02 to 0.28M ammonium phosphate (pH 6.7) in 20/80 (v/v) acetonitrile water. Recovery was approximately 80% of the applied sample.

SEQ ID NO:1 was analyzed on a DEAE-NPR anion exchange column operating on a Beckman System Gold software-controlled HPLC with two 110 B solvent delivery modules, with detection being accomplished with a model 167 UV/VIS variable wavelength detector operating at 260 and 280 nm. For analysis, elution conditions were: flowrate, 1 ml/min; linear gradient of 20 to 80% of 0.5M NaCl in 20 mM TRIS chloride (pH 8.0). Under these conditions, the retention time of SEQ ID NO:1 was 28 min. SEQ ID NO:2 was purified under similar conditions on a DEAE-NPR column.

EXAMPLE 2

Characterization of 2-5A:AS Chimeras

Figure 2:
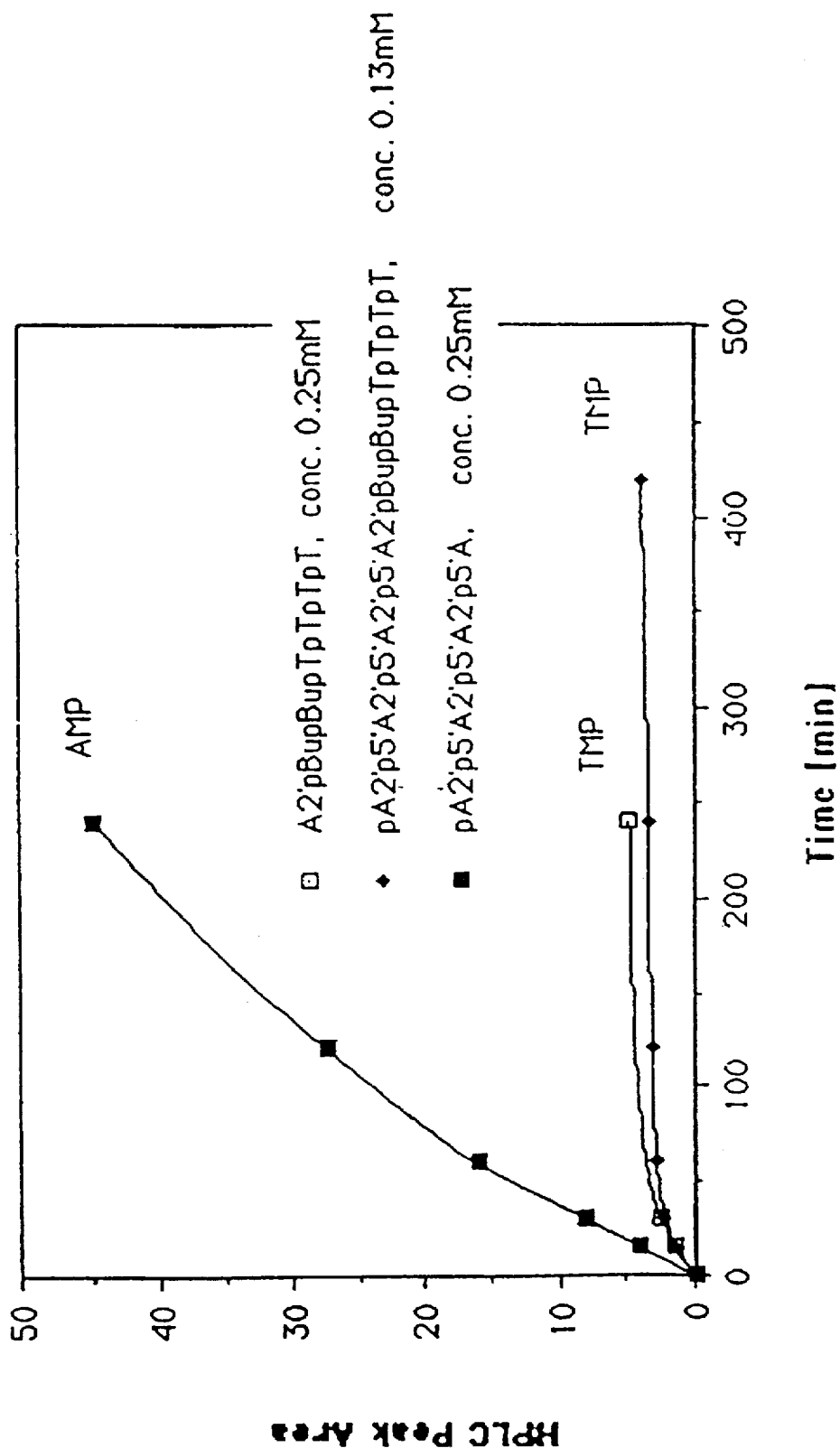
FIG. 2 is a graphic representation of the kinetics of the hydrolysis of 2-5A monophosphate as compared to the hydrolysis of chimeric 2-5A:AS molecules.

The molecules of SEQ ID NO:1, SEQ ID NO:2, Chimeric Molecule 3, and Chimeric Molecule 4 prepared as described in Example 1 were characterized by digesting approximately 0.1 to 0.2 OD of each of these oligonucleotides with 0.05 to 0.1 units of snake venom phosphodiesterase (Cooper Biomedical), 50 mM TRIS HCl, and 0.5 mM MgCl$_2$ at pH 8.0 and 37° C. for 1–3 hours. FIG. 2 shows the kinetics of the hydrolysis of 2-5A monophosphate as compared to the hydrolysis of the 2-5A:AS chimeric molecules produced in Example 1 in the presence of snake venom phosphodiesterase. Chimeric Molecule 4 (□) and 2-5A tetramer monophosphate (p5'A2'p5'A2'p5'A2'p4'A) (■) were both evaluated at initial concentrations of 0.25 mM whereas the initial concentration of Chimeric Molecule 3 (♦) was 0.13 mM.

Reaction mixtures were constituted in 50 mM Tris HCl, pH 8.0, 1 mM MgCl$_2$, containing 2.5×10$^{-3}$ units of snake venom phosphodiesterase (Cooper Biomedical). Incubation was at 37° C. Aliquots were removed at the indicated times and analyzed by HPLC. In the case of 2-5A tetramer monophosphate, the formation of 5'AMP was used as a marker of degradation, whereas for the other two oligomers 5'TMP formation was used to indicate degradation.

Digestion of SEQ ID NOS:1 and 2 and Chimeric Molecule 3 with snake venom phosphodiesterase under the above conditions gave the following respective products in the indicated ratios: SEQ ID NO:1: 5'TMP, 5'AMP, p5'A$_{linker}$ (18:3:1); SEQ ID NO:2: 5'TMP A, 5'AMP, p5'A$_{linker}$ (18:1:2:1); Chimeric Molecule 3: 5'TMP, 5'AMP, p5'A$_{linker}$ (4:3:1).

The structure of Chimeric Molecule 3 was corroborated further by proton Nuclear Magnetic Resonance: $^1$H NMR (D$_2$O)δ: 1.84 and 1.87 (both s, total of 12H, 4 thymidine CH$_3$'s), 6.05 to 6.25 [m, 4H, 4 adenosine anomeric (H-1') protons], 6.45 to 6.55 [m, 4H, 4 thymidine anomeric (H-1') protons], 7.80 to 8.40 (m, 12H, purine H-2 and H-8 protons and pyrimidine H-6 protons).

The synthetic approach shown above was based on the phosphoramidite method of solid phase DNA synthesis as modified to accommodate the incorporation of appropriate linkers and the synthesis of 2',5'-internucleotide bonds. SEQ ID NO:2, was prepared by alkaline phosphatase digestion of crude synthetic SEQ ID NO:1.

Addition of the oligothymidylate antisense component to the 2' terminus of the 2',5'-oligoadenylate protected the 2-5A moiety from degradation by snake venom phosphodiesterase (see FIG. 2). Thus, this modification presumably also would stabilize the 2',5'-oligoadenylate sequence to the 2',5'-phosphodiesterase. Other chemical modifications at the 2'-terminus of 2-5A have been shown to impart considerable resistance to degradation by phosphodiesterases and to potentiate translational inhibition and antiviral activity.

EXAMPLE 3

Snake Venom Digestion Analysis of 2-5A:AS Chimeric Molecules

Table 2 below illustrates the results of a snake venom phosphodiesterase digestion of SEQ ID NO:4-SEQ ID NO:21. The numbers under each column heading reflect the molar ratios of the digestion products that are indicated at the top of each column.

TABLE 2

| Seq. ID No.: | Digestion Product Molar Ratios: | | | | | | | |
|---|---|---|---|---|---|---|---|---|
| | dCMP | dTMP | dGMP | dAMP | AMP | A$_{link}$ | dA$_{link}$ | A |
| 4 | 7 | 7 | 3 | 2 | — | — | — | — |
| 6 | 7 | 7 | 3 | 2 | 3 | 1 | — | — |
| 7 | 3 | 2 | 7 | 7 | 3 | 1 | — | — |
| 8 | 7 | 7 | 3 | 5 | — | — | 1 | — |
| 9 | 7 | 7 | 3 | 2 | 1 | 1 | — | — |
| 10 | 7 | 7 | 3 | 2 | 2 | 1 | — | 1 |
| 11 | 7 | 7 | 3 | 2 | 6 | — | — | — |
| 12 | 7 | 6 | 3 | 3 | 3 | 1 | — | — |
| 13 | 8 | 6 | 2 | 3 | 3 | 1 | — | — |
| 14 | 7 | 3 | 3 | 6 | 3 | 1 | — | — |
| 15 | 7 | 6 | 1 | 1 | 3 | 1 | — | — |
| 16 | 6 | 4 | 1 | 1 | 3 | 1 | — | — |
| 17 | 5 | 3 | 0 | 1 | 3 | 1 | — | — |

TABLE 2-continued

| Seq. ID No.: | dCMP | dTMP | dGMP | dAMP | AMP | $A_{link}$ | $dA_{link}$ | A |
|---|---|---|---|---|---|---|---|---|
| 18 | 3 | 2 | 0 | 1 | 3 | 1 | — | — |
| 19 | 0 | 0 | 0 | 18 | 3 | 1 | — | — |
| 20 | 7 | 7 | 3 | 2 | 2 | 1 | [AMPS = 1] | * |
| 21 | 7 | 7 | 2 | 2 | 3 | 1 | 1 [DGMP-C3amine = 1] | |

*Analysis of SEQ ID NO: 20 was carried as for the other olignucleotides except that HPLC analysis also was performed employing a different elution system which allowed separation of all components, including AMPS (adenosine 5'-thiophosphate). This elution program was: 3–5% solvent B in solvent A over 20 minutes and then 5–55% solvent B in solvent A for 18 minutes where solvent A was 100 mM ammonium phosphate (pH 5.5) and solvent B was MeOH/$H_2O$ (1:1).

B. Interaction of 2-5A:AS with 2-5A-dependent RNase

It has been found that 2-5A:AS is able to activate 2-5A-dependent RNase both in vitro and in vivo. In sufficient concentrations (greater than approximately 300 nM, in the presence of concentrations of 2-5A-dependent RNase greater than those found in vivo), 2-5A:AS can cause the generalized activation of 2-5A-dependent RNase in experiments in vitro. At lower concentrations in vitro and in all in vivo experiments conducted to date, however, the interaction of 2-5A:AS and 2-5A-dependent RNase has resulted in only the specific cleavage of a target RNA molecule comprising a sense strand of RNA.

EXAMPLE 4

Interaction of 2-5A:AS and 2-5A-dependent RNase

SEQ ID NO:1, SEQ ID NO:2, Chimeric Molecule 3, and Chimeric Molecule 4 were tested for their ability to bind to 2-5A-dependent RNase in vitro. The affinity of these 2-5A:AS constructs for 2-5A-dependent RNase was established with a highly specific radiobinding assay. This radiobinding assay measured the ability of 2-5A or 2-5A analogs to compete with a $^{32}$P-labeled 2-5A probe, ppp5'A2'p5'A2'p5'A2'p5'A3'[$^{32}$P]p5'C3'p, for binding to 2-5A-dependent RNase. The nitrocellulose filter binding assay of Knight et al. (*Methods Enzymol.*, 79: 216 (1981)) was used to measure the concentrations of 2-5A or the chimeric 2-5A:AS molecule required to compete with the radiolabeled probe, ppp5'A2'p5'A2'p5'A2'p5'A3'-[$^{32}$P] p5C3'p, for binding to 2-5A-dependent RNase in a mouse liver extract.

Figure 3A:
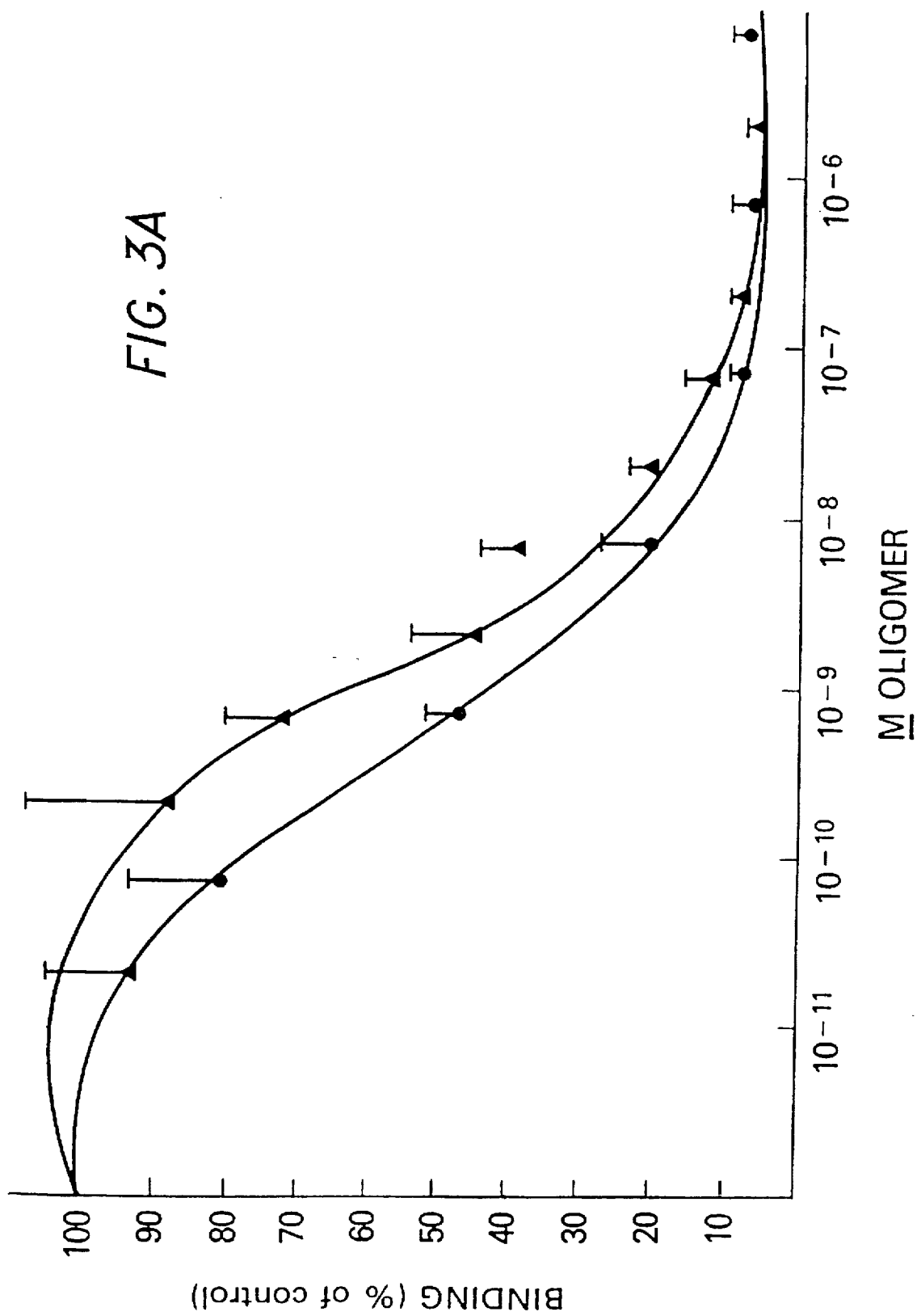
FIG. 3A is a graphical representation of the relative affinities of the chimeric molecule SEQ ID NO:1 (represented by the symbol "▲") and 2-5A (ppp5'A2'p5'A2'p5'A) (represented by the symbol "●") for 2-5A-dependent RNase.
Figure 3B:
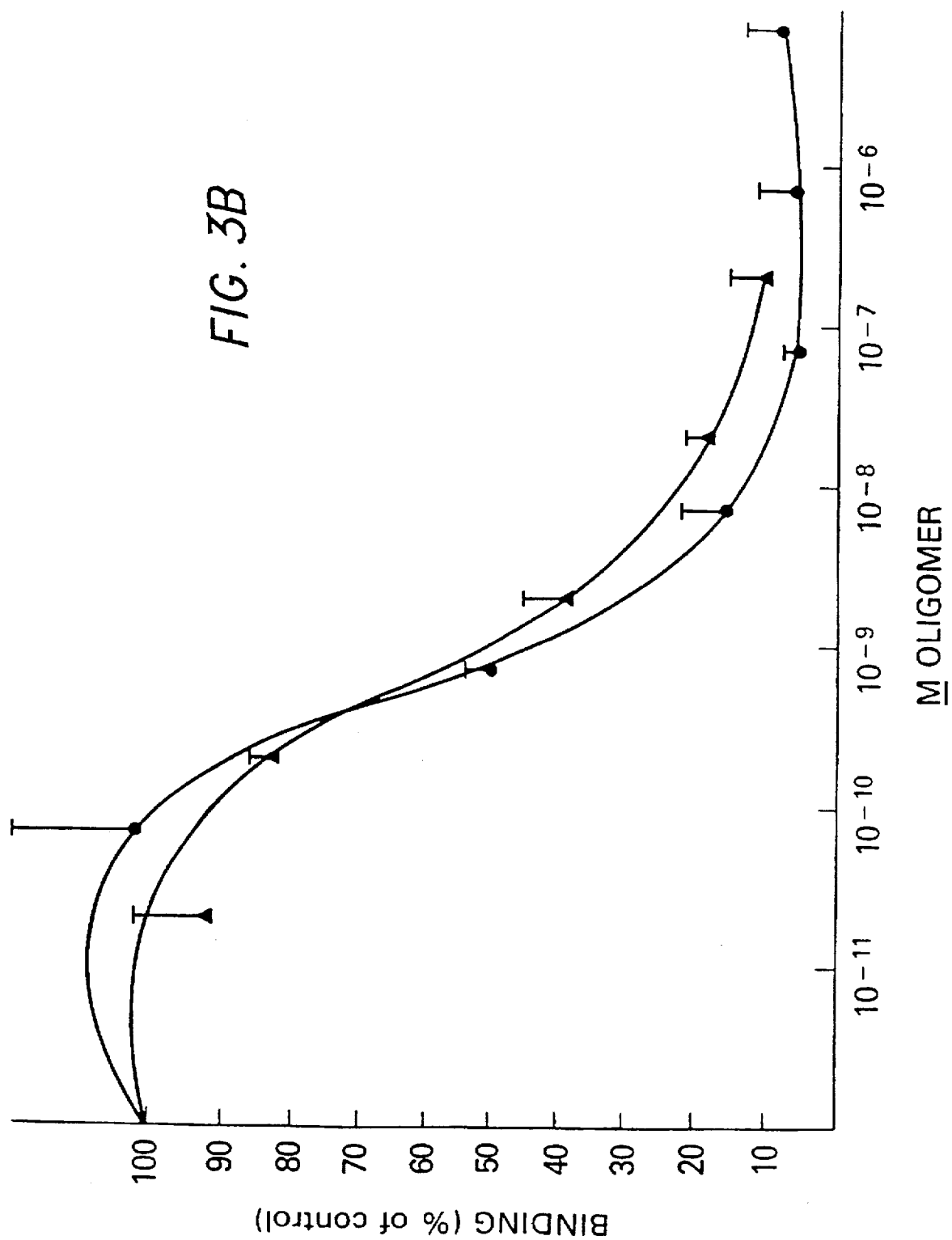
FIG. 3B is a graphical representation of the effect of the interaction of SEQ ID NO:1 with poly-A on the affinity2-5A dependent RNase for SEQ ID NO:1, where SEQ ID NO:1 annealed to poly-A is represented by the symbol "▲" and 2-5A is represented by the symbol "●".

FIGS. 3A and 3B show the relative affinities of SEQ ID NO:1 (▲) and 2-5A (ppp5'A2'p5'A2'p5'A) (●) for 2-5A-dependent RNase. A measure of 100% binding was found in the absence of any unlabeled oligonucleotide. The data for SEQ ID NO:1 and 2-5A in these figures represent the means and standard deviations from 6 and 7 assays, respectively.

The results of FIG. 3A show that chimeric 2-5A:AS constructs have the same ability to bind 2-5A-dependent RNase when compared with unmodified 2-5A. The added length of the antisense sequence compound to 2-5A did not impair endonuclease binding since there was very little, if any, decrease in the $IC_{50}$ of SEQ ID NO:1 as compared with ppp5'A2'p5'A2'p5'A. In addition, it has been found that the tetramer-tetramer adduct $pA_4:T_4$ needed a $1\times10^{-9}$M concentration to inhibit probe binding to 2-5A-dependent RNase by 50% ($IC_{50}$). A similar $IC_{50}$ of $7\times10^{-10}$M was obtained for 2-5A itself (data not shown).

As shown in FIG. 3B, when the antisense region of the chimeric molecule was annealed to its complementary sequence, there also was no significant effect on the ability of the construct to bind to 2-5A-dependent RNase. Thus, when SEQ ID NO:1 was mixed in various concentrations with excess poly(A), there was no significant change in the binding affinity to 2-5A-dependent RNase as compared with the unannealed SEQ ID NO:1 or with 2-5A trimer itself (FIG. 3B).

In addition, when a radiobinding assay was performed on an aliquot of the solution that had been used to determine the $T_m$ of the SEQ ID NO:1/poly(A) complex, an identical binding curve was obtained (data not shown).

Figure 4:
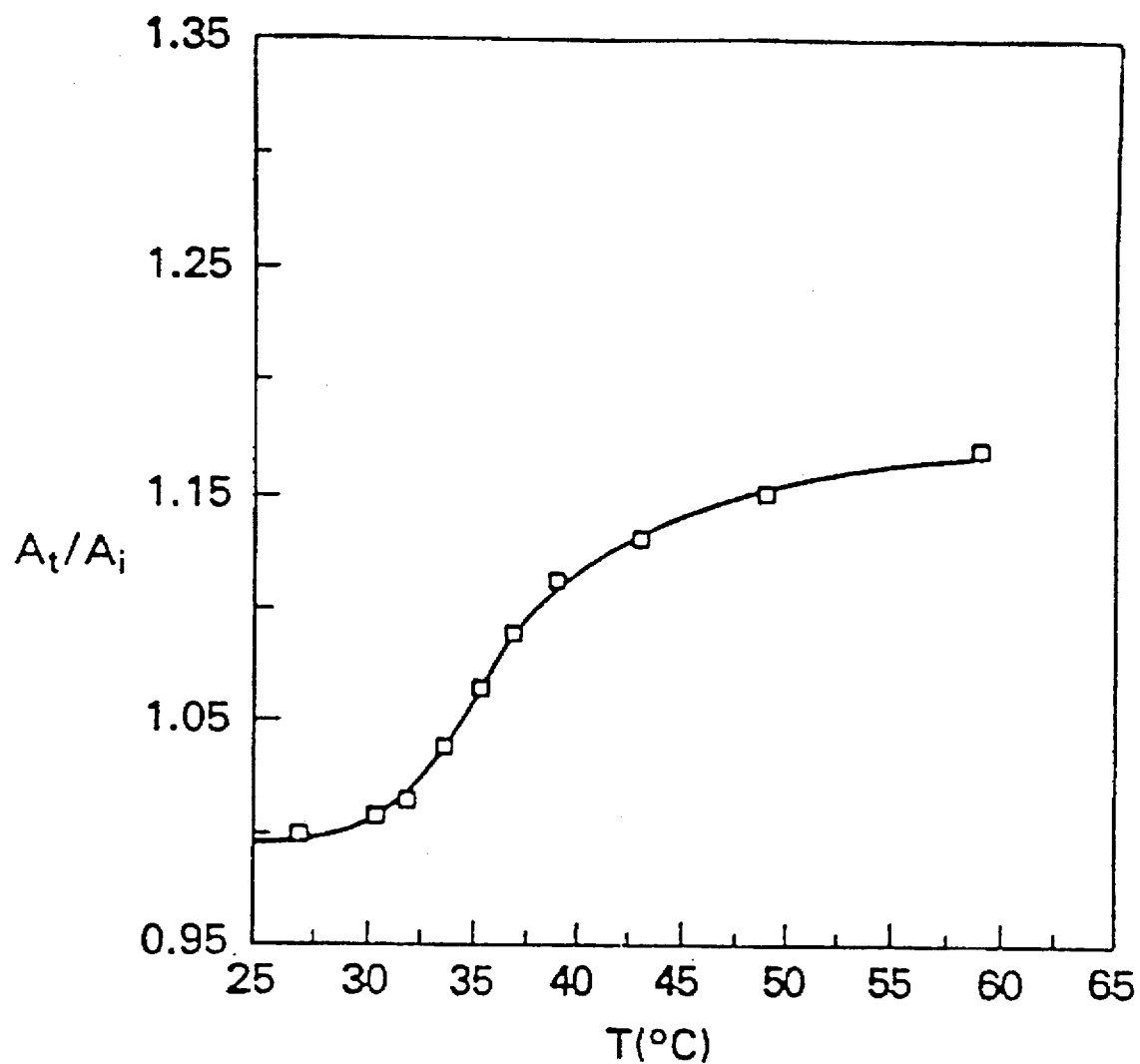
FIG. 4 is a graph which shows an absorbance-temperature profile of an equimolar mixture of poly(A) and SEQ ID NO:1 as determined in $KH_2PO_4$ buffer (40 mM, pH 7.0).

We also compared the melting temperature of poly (A) with the melting temperature of SEQ ID NO:1 (FIG. 4). For this experiment, 1000 µL of $3.2\times10^{-6}$ M poly(A) in $KH_2PO_4$ buffer (pH 7.0, 40 mM) was mixed with 1000 µL of $2.9\times10^{-6}$M SEQ ID NO:1 in $KH_2PO_4$ buffer, and the resulting mixture was incubated at 4° overnight before determination of melting temperature. At/Ai refers to the ratio of absorbance ($A_t$) at a given temperature compared to the absorbance ($A_i$) at the initial temperature (25°–30°). No attempt was made to determine complex stoichiometry (2- or 3-stranded). Under similar conditions, an equimolar mixture of poly(A) and oligo(dT)$_{20}$ gave a complex with a $T_m$ of 40° (data not shown).

The effect of the 2-5A moiety of SEQ ID NO:1 on the ability of the $dT_{18}$ region to anneal with its complementary poly(A) sequence as determined from UV absorbance-temperature profiles is shown in FIG. 4. A $3.2\times10^{-6}$ M solution of poly(A) was mixed with a $2.9\times10^{-6}$ M solution of SEQ ID NO:1 in a buffer of 40 mM $KH_2PO_4$ (pH 7.0), resulting in a hypochromicity of 17%, and the complexes which were found to have formed a melting temperature ($T_m$) of approximately 38° C. in the same buffer (data not shown). Under the same conditions, the complex $dT_{20}$/poly (A) had a $T_m$ of 40° C., in good agreement with previously published values.

C. Inducing Specific Cleavage of RNA with 2-5A:AS

When administering 2-5A:AS according to the methods of the present invention in order to induce the specific cleavage of a particular molecule of RNA, 2-5A:AS should be added in concentrations of between about 0.01 µM and 10 mM, preferably between about 0.1 µM and 100 µM, and most preferably between about 1.0 µM and 5.0 µM. As is known to those of skill in the art, the optimal concentration of a chimeric molecule for cleaving a target molecule of RNA in a particular application will depend on the concentration of the RNase used, the concentration of the target RNA molecule, as well as on other conditions. Thus, one of skill in the art will be able to determine the optimal concentration of 2-5A:AS to be used in a given application through the application of routine experimentation.

EXAMPLE 5

Specific Cleavage of RNA by SEQ ID NO:1

To determine the ability of the 2-5A:AS chimeric molecule SEQ ID NO:1 to induce site-directed RNA cleavage, a target RNA was constructed having an internal 3',5'-oligo (rA) tract. Hybridization between the $(dT_{18})$ in SEQ ID NO:1 with the oligo(rA) in the target RNA attracts 2-5A-dependent RNase to the target RNA, resulting in a highly specific cleavage event. The experimental target, TAR:$A_{25}$:vif RNA, was produced in vitro from a pSP64-derived plasmid containing a partial cDNA for the HIV vif protein interrupted with 25 adenylyl residues. A control TAR:vif RNA was constructed with the $A_{25}$ tract deleted. These RNA species, which lack 3'-poly(rA) tails, were radiolabeled at their 3'-termini with [5'-$^{32}$P]-pCp by T4 RNA ligase and gel purified prior to the assay.

Figure 5:
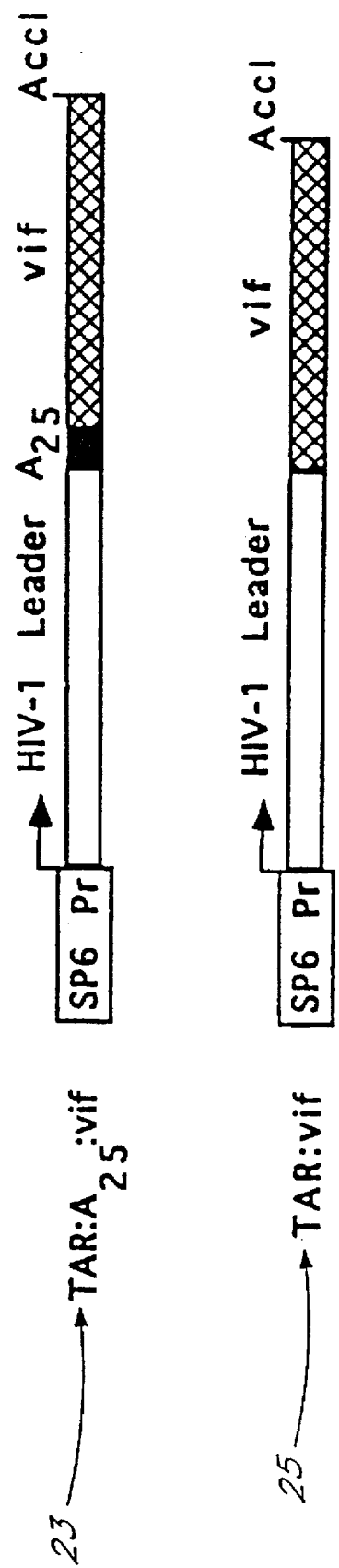
FIG. 5 is a schematic representation of the sequences contained in the AccI-digested plasmid fragments used in the detailed description to illustrate the present method (TAR:$A_{25}$:vif and TAR:vif).

1. Producing TAR:$A_{25}$:vif RNA Target RNA The plasmid pSP6/TAR:$A_{25}$:vif (23, FIG. 5) was made by first subcloning a portion of HIV-1 vif cDNA (HindIII and EcoRI fragment) from plasmid pSP2 into a pSP64HIV+1 to +80 vector obtained after HindIII and EcoRI digestion of the plasmid HIV+1 to +231/IFN$_\gamma$. An insert of $dA_{25}$:$dT_{25}$ was obtained by annealing two chemically synthesized complementary oligonucleotides having $dA_{25}$ and $dT_{25}$ sequences flanked by BssHII and NdeI restriction site linkers. The $dA_{25}$:$dT_{25}$ insert was then cloned into the corresponding cohesive ends of the BssHII and NdeI digested plasmid.

The resulting plasmid, pSP6/TAR:$A_{25}$:vif contained the SP6 promoter followed by 262 bp of the HIV-1 leader sequence (abbreviated as "TAR" because it begins with the transactivation responsive sequence), followed by the $dA_{25}$ insertion, followed by a 495 base pair coding sequence for the HIV-1 vif protein. Plasmid pSP6/TAR:vif (25, FIG. 5) was made by digesting plasmid pSP6/TAR:$A_{25}$:vif with BssHII and NdeI and ligating the cut ends after filling in with Klenow fragment. Plasmids pSP6/TAR:$A_{25}$:vif and pSP6/TAR:vif were linearized with AccI restriction endonuclease (within the vif coding sequence) and transcribed with SP6 RNA polymerase by well known methods.

In vitro synthesized RNAs were labelled at their 3' termini with cytidine 3',5'-[5-$^{32}$P] bisphosphate with T4 RNA ligases (Pharmacia) and the RNAs were purified from sequencing gels. TAR:$A_{25}$:vif RNA and TAR:vif RNA are 500 and 471 nucleotides in length, respectively.

2. Demonstrating Specific Cleavage of Target RNA

The 2-5A:AS strategy for site-directed RNA cleavage was next tested in a cell-free system consisting of a postribosomal supernatant fraction of human lymphoblastoid Daudi cells. An extract of these cells exhibited basal levels of 2-5A-dependent RNase as detected by a radiobinding assay using a $^{32}$P-labeled 2-5A analog (Knight, et al., *Methods Enzymol*, 79:216 (1981)).

Daudi cell extracts prepared with dounce homogenization were made by the well known method of Wreschner, et al. in a buffer containing 40 mM KCl; 10 mM HEPES pH 7.5; 2.5 mM magnesium acetate; 0.5 mM ATP; 2.5% glycerol and 2.0 mM mercaptoethanol. The extract used in the RNA cleavage assays was the supernatant of a 100,000 x g centrifugation of cell extract. About 100 nM radiolabeled RNA (approximately 25,000 counts/min/assay) was incubated with oligonucleotides at 30° C. in extract (10 µl) supplemented with 75 mM KCl in a final volume of 20 µl. Reactions were terminated and the RNA was extracted with phenol/chloroform. The RNA was then ethanol precipitated and redissolved in sterile water and an equal volume of formamide gel sample buffer. Cleavage products were analyzed in 6% polyacrylamide/8M urea gels (30x 40x 0.04 cm).

The cleavage reaction was performed after adding SEQ ID NO:1 and purified radiolabeled TAR:$A_{25}$:vif RNA to the Daudi cell extract (without preannealing) followed by incubation at 30° C. In the absence of added oligonucleotide, the TAR:$A_{25}$:vif RNA was degraded with a half-life of about 90 minutes.

An experiment was conducted to analyze (A) the in vitro transcription of AccI restriction endonuclease-digested plasmids containing TAR:$A_{25}$:vif and TAR:vif sequences and (B) the specific cleavage of TAR:$A_{25}$:vif RNA induced by SEQ ID NO:1 (100 nM) in extracts of Daudi cells as a function of time. The breakdown of TAR:$A_{25}$:vif RNA (intact RNA) was proportional to the appearance of the specific cleavage product. Data was obtained by running a gel with the products of the experiment and then making an autoradiogram of the dried gel. The autoradiogram was then subjected to image analysis with a video camera (Sierra Scientific) and the QUICKCAPTURE© (Marlboro, Mass.) and IMAGE© computer programs run on a MACINTOSH IIci™ computer. The percentage of RNA shown in FIG. 6 was based on the sum of the intact RNA and the specific RNA cleavage product.

Cleavage of TAR:$A_{25}$:vif RNA (about 100 nM) as a function of SEQ ID NO:1 concentration was also measured. The cleavage reaction was allowed to continue for 30 minutes in Daudi cell extract at 30° C. The levels of the specific cleavage products (relative peak areas) were determined from an autoradiogram as described in relation to FIG. 6 above. The results shown in FIGS. 6 and 7 were reproduced three times.

Figure 6:
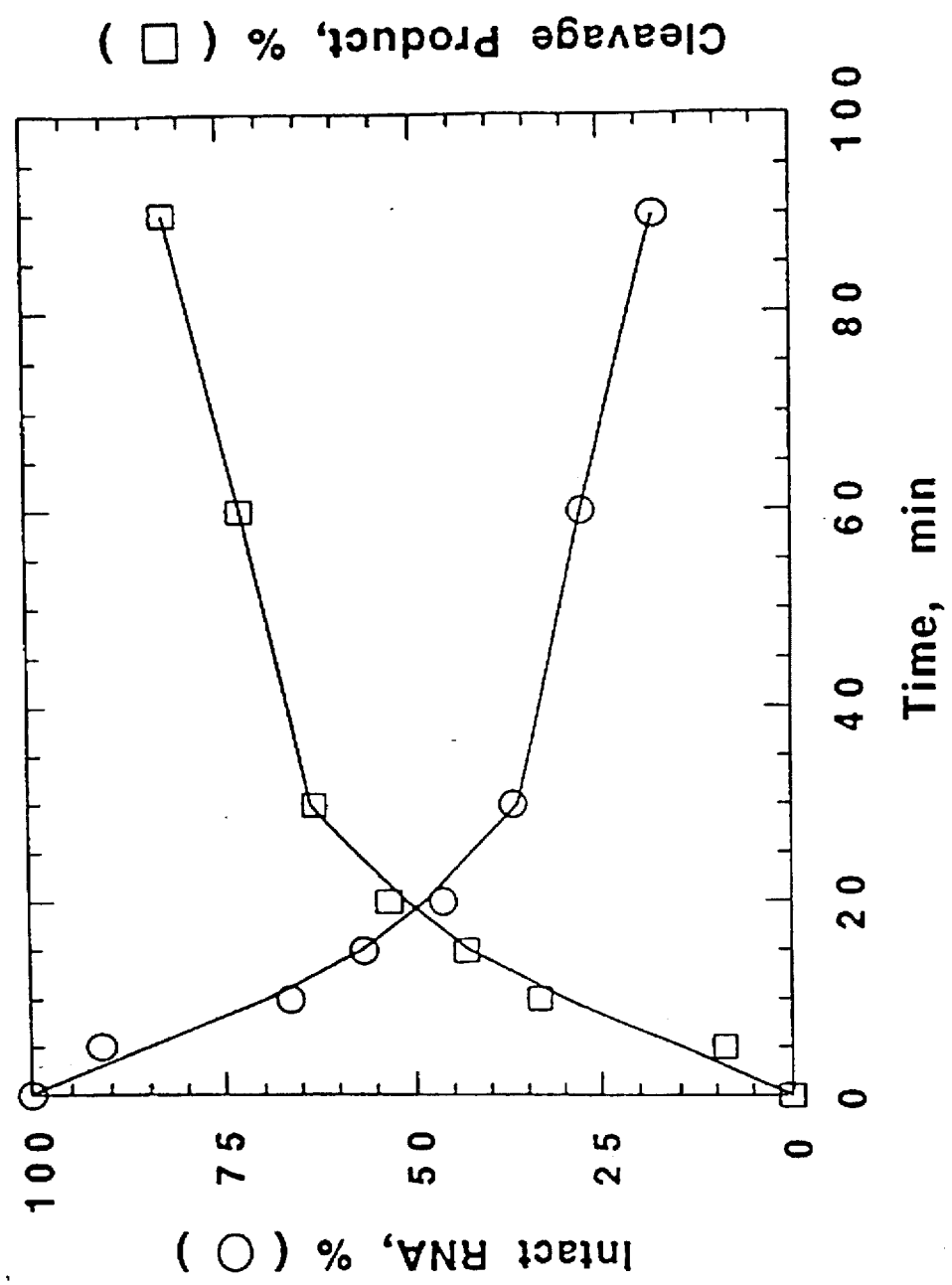
FIG. 6 is a graph showing that the breakdown of TAR:$A_{25}$:vif RNA (intact RNA) in the presence of 2-5A:AS and 2-5A-dependent RNase is proportional to the appearance of the specific cleavage product.
Figure 7:
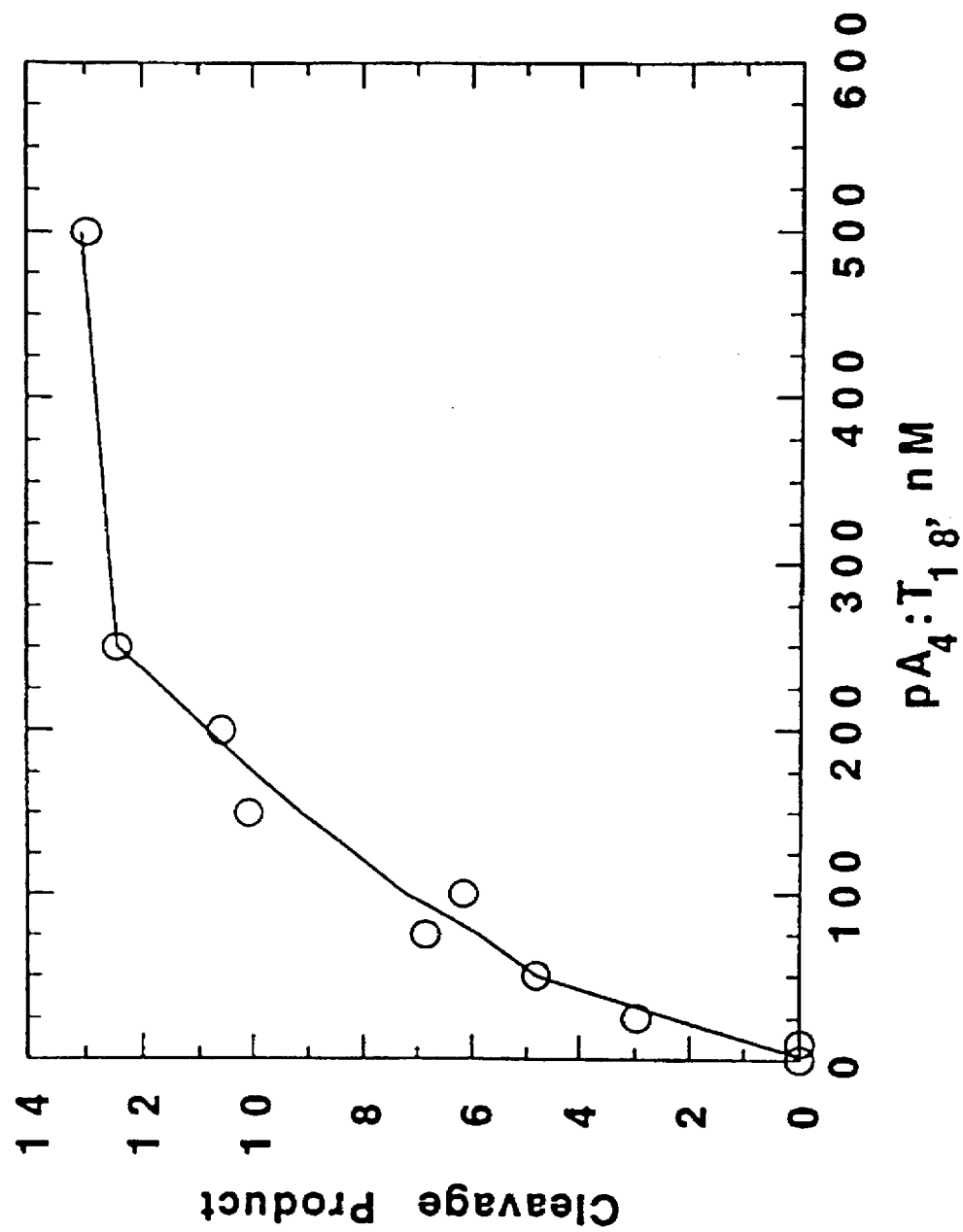
FIG. 7 is a graph showing the cleavage of TAR:$A_{25}$:vif RNA (about 100 nM) as a function of the concentration of SEQ ID NO:1, where the cleavage reaction was for 30 minutes in Daudi cell extract at 30° C., and the levels of the specific cleavage product (relative peak areas) were determined from an autoradiogram of a gel.

Remarkably, the addition of the 2-5A:AS SEQ ID NO:1 to the cell-free system resulted in the nearly quantitative conversion of the intact RNA to a specific cleavage product. Breakdown to the cleavage product could be seen clearly after as little as 5 minutes of incubation. Quantitation of these results showed that the loss of the intact RNA was proportional to the production of the cleavage product, suggesting that the specific cleavage reaction accounted for essentially all of the breakdown reaction (FIG. 6). There was 50% breakdown to the specific cleavage product after 20 minutes of incubation in the presence of SEQ ID NO:1 (FIG. 6). Therefore, the addition of SEQ ID NO:1 to the Daudi cell extract increased the rate of breakdown of the TAR:$A_{25}$:vif RNA more than four-fold. To determine the optimal level of SEQ ID NO:1 for the cleavage reaction, its concentration was varied against a constant amount of TAR:$A_{25}$:vif RNA (FIG. 7). The cleavage reaction was observed with as little as 25 nM and was optimal at 250 nM of SEQ ID. NO:1 (FIG. 7).

EXAMPLE 6

Characterization of the Cleavage Products of 2-5A-dependent RNase

To determine the exact sites of cleavage of the TAR:$A_{25}$:vif RNA induced by SEQ ID NO:1, a primer-extension DNA synthesis reaction was performed on the RNA cleavage products with reverse transcriptase. Consistent with previous results, levels of intact RNA, as measured by the full-length primer extension products, were greatly reduced after incubating the cell-free system in the presence of SEQ ID NO:1 in comparison to incubating RNA in the absence of added oligonucleotides, or with SEQ ID NO:2 or with (2'-5')$p_3A_3$.

A primer extension assay was used as described by Driscoll, et al. (*Cell*, 58:519 (1989)) except that all four dNTPs were included. DNA sequencing of plasmid pSP6/TAR:A$_{25}$:vif was with the same primer using Sequenase version 2.0 (United States Biochemical) and $^{35}$S-dATP. The sequence of the primer was 5'-TCCTGTATGCAGACCCCAATATGTTGTTAT-3' (SEQ ID NO:3). Results were reproduced from two separate sets of RNA cleavage reactions.

The cleavage sites of the RNA subjected to the RNA cleavage reactions described above were determined by comparing the migration of the primer extension products and DNA sequencing products performed with the same primer annealed to the plasmid containing the TAR:A$_{25}$:vif sequence. Interestingly, the results showed that SEQ ID NO:1 induced multiple cleavages within the oligo(rA) tract of the RNA. SEQ ID NO:2 appeared to be very weakly active in this assay compared SEQ ID NO:1, once again indicating the importance of the 5'-phosphoryl moiety of 2-5A for activation of 2-5A-dependent RNase. There were no specific cleavage products in the absence of oligonucleotide or with p$_3$A$_3$. Previous reports indicate that unmodified 2-5A stimulates 2-5A-dependent RNase to cleave RNA on the 3'-side of UN sequences, where N stands for any nucleotide. It has been suggested that the sequence-specificity of 2-5A-dependent RNase for uridine-rich RNA may be a function of the complementary adenosine residues in 2-5A. These results indicate that redirecting the binding of 2,5A-dependent RNase to a particular RNA sequence alters its cleavage specificity.

D. Factors which Influence the Reaction of 2-5A:AS

A number of factors influence the specificity and efficacy of the 2-5A:AS reaction which causes the degradation of a target RNA molecule. These various factors are discussed in detail below.

1. The RNase Used Must be 2-5A-dependent RNase

In the preferred embodiment of the present invention, in which the chimeric molecule used is 2-5A:AS, 2-5A-dependent RNase must be present in order for the chimeric molecule to be able to cleave a target RNA molecule. This has been established through control experiments showing that the cleavage reaction observed when performing the methods of the present invention is due to the targeted degradation of RNA by 2-5A-dependent RNase and not by some other nuclease. In these experiments, which were performed under conditions similar to those of Example 5 above, several different chimeric molecules and agents were added to reaction mixtures containing 2-5A-dependent RNase and a TAR:A$_{25}$:vif RNA substrate. Specific cleavage of the substrate was observed in vitro only after incubation with the chimeric molecule SEQ ID NO:1. Through the examination of the remaining control samples tested, the cleavage reaction was determined to be dependent on a functionally active species of 2-5A. Of course, if an RNase besides 2-5A-dependent RNase is used in the present methods, an activator of that RNase would be joined in a chimeric molecule rather than joining a molecule of 2-5A. The efficient activation of human 2-5A-dependent RNase was also found to require a 2',5'-oligonucleotide with at least one 5'-phosphoryl group. The non-5'-phosphorylated compound, SEQ ID NO:2, failed to produce detectable amounts of the specific cleavage product in this experiment.

Additional proof for the critical role of the 2-5A-dependent RNase in the specific cleavage reaction was provided through the use of the. 2-5A analog-inhibitor, ppp5'I2'p5'A2'p5'A, an inosine-substituted derivative of 2-5A. When ppp5'I2'p5'A2'p5'A (2.0 µM) was present in an assay similar to that of Example 5, it completely prevented the ability of SEQ ID NO:1 to cause specific cleavage of the target RNA. This is believed to be due to the inhibition of 2-5A-dependent RNase by ppp5'I2'p5'A2'p5'A.

Furthermore, when 50–150 nM SEQ ID NO:6 was incubated in the presence of PKR RNA (100 nM) at 37° C. for 30 minutes in the presence of 2-5A-dependent RNase, complete degradation of the PKR RNA was observed (see Example 7 below for a discussion of PKR). Moreover, when up to 2 µM SEQ ID NO:6 was incubated in the presence of PKR RNA (100 nM) at 37° C. for 30 minutes in the absence of 2-5A-dependent RNase, almost no degradation of the PKR RNA was observed. These data prove that 2-5A-dependent RNase is capable of effecting the cleavage reaction in the 2-5A-antisense method. The data also indicates that the RNase activated by the RNase activator moiety of a chimeric molecule should be present in a system when a chimeric molecule is used to cleave a target RNA molecule according to the present methods.

2. The 2-5A:AS Must Bind to Target RNA

It has also been found that 2-5A:AS must bind to a target molecule of RNA in order to specifically cleave that molecule. In order to show this, an experiment was performed showing that the specific cleavage of a TAR:A$_{25}$:vif RNA substrate by SEQ ID NO:1 was dependent on the binding of SEQ ID NO:1 to the oligo(rA) tract of the target RNA. In this experiment, an excess of oligo(dT)$_{20}$ was added to the cell extract together With SEQ ID NO:1 in an attempt to block specific breakdown of the TAR:A$_{25}$:vif RNA. The oligo(dT)$_{20}$ completely prevented the cleavage reaction, suggesting that binding of the 2-5A:AS to the target RNA was a prerequisite for targeted cleavage.

Furthermore, the 2-5A tetramer p5'A2'p5'A2'p5'A2'p5'A fused to oligonucleotide sequences which were unrelated to those in the target RNA failed to produce the specific product of the cleavage of the oligo(rA) tract of TAR:A$_{25}$:vif RNA. This shows that specific binding of the antisense moiety of the chimeric molecule to a target RNA molecule is necessary for the specific cleavage of that molecule. When Chimeric Molecule 3 was added to a reaction mixture containing TAR:A$_{25}$:vif RNA and 2-5A-dependent RNase, it too failed to induce the specific cleavage reaction because the antisense chain was too short to permit a stable hybrid to form with the oligo(rA) tract in the target RNA.

In addition, SEQ ID NO:1 (at 0.2 or 1.0 µM) failed to yield a specific cleavage in TAR:vif RNA which lacked the oligo(rA) tract, thus further demonstrating the necessity for hybridization to a complementary region on the target substrate. Therefore, competition, sequence variation, sequence deletion, and chain length experiments all point to the critical role of the antisense portion of the chimeric 2-5A:AS molecule in producing specific cleavage of a sense strand of RNA.

Further evidence that the antisense moiety of 2-5A:AS must anneal to a target molecule of RNA in order to cleave it is provided by the fact that 2-5A:AS molecules having highly mismatched antisense oligonucleotide moieties are not effective to cleave a target RNA molecule. In an in vivo assay of HeLa cells, 2 µM SEQ ID NO:6 and the same amount of SEQ ID NO:14 was added to separate cultures of cells. SEQ ID NO:14 is a 2-5A:AS molecule having an antisense oligonucleotide moiety sequence similar to that of SEQ ID NO:6 but differing at 10 positions, thus having mismatches with respect to PKR RNA. The treated cells were incubated for 4 hours, and a PCR assay (described elsewhere herein) was then performed to gauge the amount of PKR RNA remaining in such cells. While SEQ ID NO:6 greatly reduced levels of PKR RNA from the cells, the mismatched SEQ ID NO:14 contained about the same amount of PKR RNA as control cells to which no oligonucleotides were added. Thus, it is believed that the high degree of non-complementarity prevented SEQ ID NO:14 from annealing to its target RNA molecule with sufficient stability to direct the specific cleavage of that target RNA molecule.

In an in vitro assay using SEQ ID NO:14, this chimeric molecule was unable to mediate the specific cleavage of PKR RNA. In this assay, 100 nM PKR RNA was incubated with 150 nM of SEQ ID NO:14 for 30 minutes at 37° C. in the presence of 2-5A-dependent RNase, and no cleavage of the PKR RNA was observed. This finding suggests that chimeric molecules having highly mismatched antisense oligonucleotide moieties do not cause the selective cleavage of target RNA molecules.

Other chimeric molecules having mismatched antisense oligonucleotide moieties but having greater complementarity would be expected to be more effective in vitro and in vivo when used in the methods of the present invention. For example, SEQ ID NO:12, having only one mismatched base pair, would in most cases be expected to mediate cleavage activity similar to that of SEQ ID NO:6. SEQ ID NO:13, having 4 base pair mismatches out of 19 antisense oligonucleotide moiety bases would also be expected to work, although perhaps less effectively. One of skill in the art would be able to determine whether a particular mismatched antisense moiety would be able to anneal sufficiently with a target RNA molecule in order to be effective in the present methods by the use of current knowledge in the field. For example, the number of mismatches, the amount of GC hydrogen bonding among the complementary base pairs, and the hybridization conditions under which the cleavage reaction was being performed can be considered. A more definitive determination of the ability of a particular mismatched antisense oligonucleotide moiety to bind to a target RNA molecule and to cleave that molecule can then be made through the use of routine experimentation.

Chimeric molecules having antisense oligonucleotide moieties that are shorter than those described herein would also be expected to display a lesser ability to mediate the cleavage of a target RNA molecule due to a decrease in binding ability. This lower effectiveness should be similar to the decrease in effectiveness observed as the number of mismatches in an antisense oligonucleotide moiety increases. Thus, it is expected that SEQ ID NO:6 and SEQ ID NOS:15–18 would fall in to the following pattern of effectiveness, in decreasing order: SEQ ID NO:6 (having an antisense oligonucleotide moiety 19 nucleotides long)>SEQ ID NO:15 (15 nucleotides long)>SEQ ID NO:16 (12 nucleotides long)>SEQ ID NO:17 (9 nucleotides long)>SEQ ID NO:18 (6 nucleotides long).

However, this decrease in effectiveness may not necessarily be observed when the product dissociation rate (the rate at which an antisense oligonucleotide moiety dissociates from cleaved RNA) is rate limiting. In such cases, chimeric molecules with shorter antisense oligonucleotide moieties may be more effective than those with longer antisense oligonucleotide moieties, because such shorter molecules will be able to bind to a targeted RNA molecule, effect its cleavage, and then dissociate faster than molecules with longer antisense oligonucleotide moieties. The use of shorter antisense oligonucleotides may also alter the specificity of the present methods, though.

EXAMPLE 7

Demonstration of the Specificity of the Antisense Oligonucleotide Moiety of 2-5A:AS To demonstrate that the antisense oligonucleotide portion of 2-5A:AS specifically selects a target RNA molecule with which it is complementary for cleavage in the presence of unrelated RNA, an RNA mixing experiment was performed. The target RNA chosen for this experiment was mRNA which codes for the PKR protein. PKR is an interferon-inducible protein which regulates protein synthesis (Hovanessian, A. G. *J. Interferon Res.*, 9:641–647 (1989)) and which functions as a tumor suppressor factor (Meurs et al., *Proc. Natl. Acad. Sci. USA*, 90:232–236 (1993); Koromilas et al., *Science*, 257:1685–1689 (1992)). At the protein synthesis level, PKR phosphorylates the α subunit of protein synthesis initiation factor eIF-2, a component of the ternary complex, eIF-2:GTP:MET-tRNAi. When the 80S ribosome is formed, the GTP in the ternary complex is hydrolyzed allowing release of eIF-2α:GDP. The subsequent exchange of GTP for GDP on the eIF-2α is catalyzed by eIF-2B (GEF), a rate limiting factor in protein synthesis initiation (reviewed by Safer et al., *Cell* 33:7–8 (1983)). Phosphorylation of eIF-2α inhibits the eIF-2B catalyzed recycling reaction resulting in the cessation of protein synthesis due to an accumulation of inactive eIF-2:GDP complex. In addition, expression of PKR cDNA reduces replication of encephalomyocarditis virus providing convincing evidence that the kinase is involved in the antiviral activity of interferon (Meurs et al., *J. Virology*, 66:5805–5814 (1992)). Furthermore, the tumor suppressor function of PKR has been demonstrated (Meurs et al., 1993; Koromilas et al., 1992). Mutants of PKR apparently function as dominant negative inhibitors of endogenous PKR activity, leading to the formation of tumors in mice.

Figure 8:
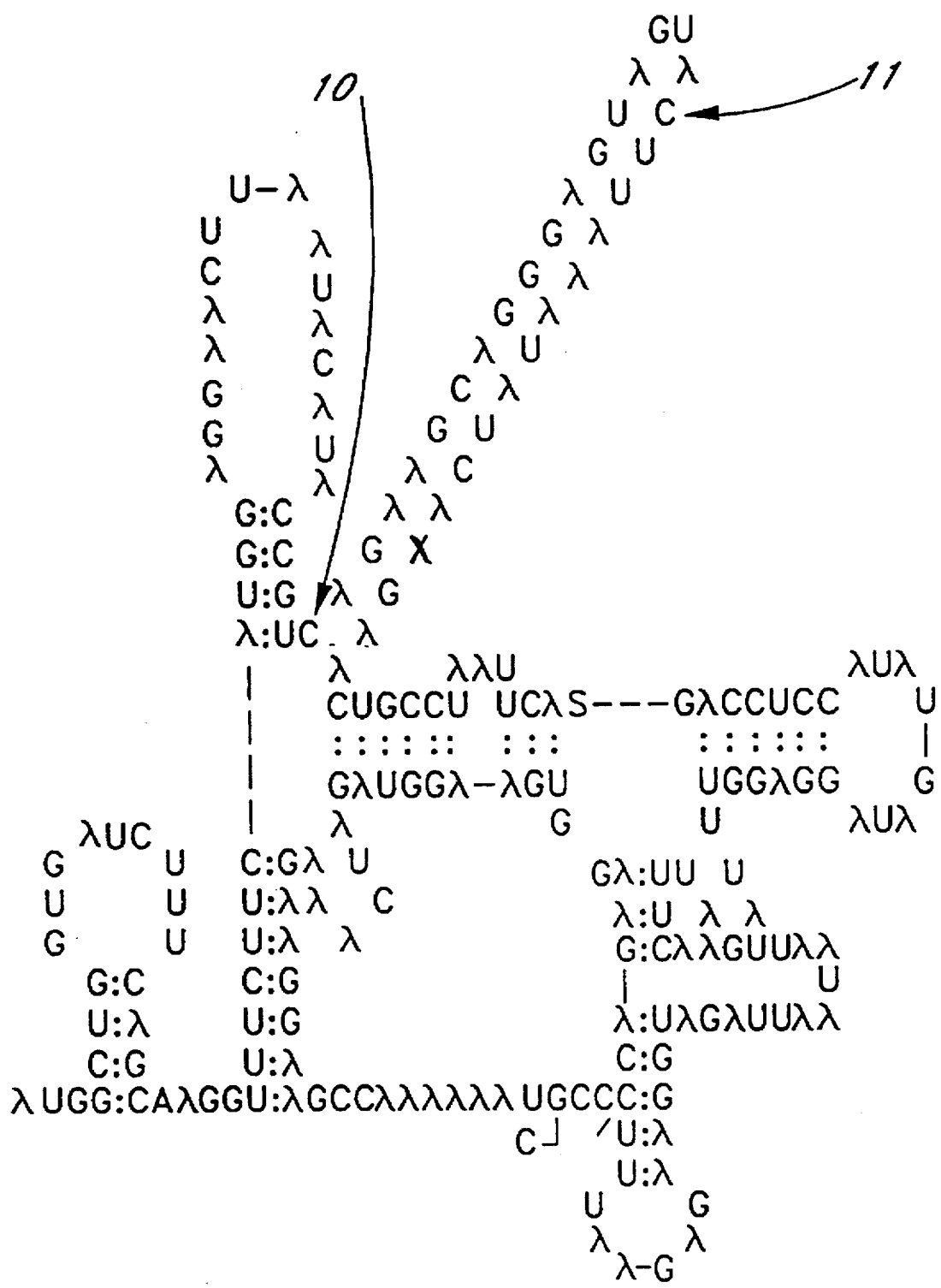
FIG. 8 illustrates the predicted secondary structure for nucleotides 1 to 200 (SEQ ID NO:22) of the coding sequence for PKR. The RNAFOLD computer program was used to determine the illustrated secondary structure.

The PKR mRNA site chosen as the target of the 2-5A:AS chimeric molecule was 55–73 nucleotides from the start codon of the PKR mRNA in a region predicted by computer analysis to be single stranded (see FIG. 8). The following 2-5A:AS chimeric molecule directed against PKR mRNA thus was selected for synthesis: p5'A2'p5'A2'p5'A2'p5'A2'-CC$_4$-p-C$_4$-p5'GTACTA CTCCCT GCTTCT G3' (SEQ ID NO:6).

The 2',5'-oligoadenylate moiety and the 3',5'-deoxyribonucleotide antisense sequence of this molecule were linked by two 1,4-butanediol molecules linked through phosphodiester bonds. PKR mRNA and mRNA to the HIV vif protein were synthesized by in vitro transcription of cDNAs. These RNAs were then 5'-labeled with γ-$^{32}$P-ATP and polynucleotide kinase and the resulting radiolabeled RNAs were purified from sequencing gels.

Mixtures of the two RNA species were first incubated with increasing levels of p(A2'p)$_3$A-antiPKR (SEQ ID NO:6) for about 10 minutes. In separate reaction mixtures, the two RNA species were exposed to 0 nM, 5 nM, 10 nM, 20 nm, 50 nM, 100 nM, 200 nM, 300 nM, and 500 nM concentrations of SEQ ID NO:6.

Purified recombinant 2-5A-dependent RNase (100 ng per 20 μl reaction mixture) was then added to each mixture, and the reaction mixtures were incubated for 5 minutes at 37° C.

The preferential cleavage of the PKR mRNA was clearly demonstrated, with observable levels of cleavage beginning at about 10–20 nM concentrations. Half of the PKR mRNA was degraded in the presence of 25 to 50 nM SEQ ID NO:6. In contrast, 200 to 300 nM of SEQ ID NO:6 was required to induce 50% degradation of the vif mRNA. At this concentration, the 2-5A moiety of the 2-5A:AS molecules probably induced the generalized activation of 2-5A-dependent RNase, which in this experiment was present in concentrations far in excess of the concentrations of 2-5A-dependent RNase found in mammalian cells. Therefore, SEQ ID NO: 6 activated and selectively recruited the 2-5A-dependent RNase to cleave PKR mRNA.

3. The Antisense Moiety of the 2-5A Molecule Must be Present

It has been further found that the antisense moiety of the 2-5A:AS molecule must be present in order to specifically cleave a target RNA molecule. This property of the molecule was determined by experiments employing unmodified 2-5A. The addition of 2-5A tetramer 5'-monophosphate or tetramer triphosphate ($p_3A_4$) to the cell-free system described in Example 5 did not induce the specific cleavage of TAR:$A_{25}$:vif RNA observed with SEQ ID NO:1. In a series of experiments, one set of reactions was performed in the cell-free system containing TAR:$A_{25}$:vif RNA while another set of reactions was performed with TAR:vif RNA as a substrate. These reactions were performed both with and without Daudi extract. Oligonucleotides were present at 100 nM, except for $dT_{20}$ (1.0 µM), $pA_4$ (1.0 µM), $p_3A_4$ (1.0 µM), $p_3IAA$ (2.0 µM), and $pA_4$:$T_{18}$ (0.2 µM and 1.0 µM). Incubation was for 30 minutes at 30° C. in Daudi extract. These experiments were reproduced three times. None of these experiments exhibited the site specific cleavage observed when SEQ ID NO:1 was added to a mixture containing TAR:$A_{25}$:vif RNA.

The specificity of 2-5A:AS chimeric molecules was further established through in vitro experiments using SEQ ID NO:6 and SEQ ID NO:7. The substrate, PKR RNA, was produced in vitro from a plasmid containing the PKR cDNA (a gift of Dr. B. R. G. Williams) by transcribing the plasmid PKR cDNA with a phage RNA polymerase. Cleavage of the PKR mRNA (labeled at its 5'-terminus with $\gamma$-$^{32}$P-ATP and polynucleotide kinase) by the complex of 2-5A:AS and 2-5A-dependent RNase was determined in sequencing gels. In these experiments, about 100 nM PKR RNA incubated for 5 minutes at 37° C. with various reaction mixtures carrying the following concentrations of chimeric molecules: 1) 0 nM, 25 nM, 50 nM, 150 nM, 250 nM, and 500 nM of SEQ ID NO: 7; and 2) 0 nM, 25 nM, 50 nM, 150 nM, 250 nM, and 500 nM of SEQ ID NO:6.

The loss of the intact RNA in the sequencing gels was accurately measured using a PhosphorImager (Molecular Dynamics, Inc.). Because multiple cleavages are thought to occur within each target sequence, the most important measurement was the rate at which the concentration of intact RNA decreased. The sense orientation chimeric molecule, SEQ ID NO:7 was only very weakly active against PKR mRNA. Indeed, even at 500 nM, SEQ ID NO:7 induced less than 30% degradation of the PKR RNA. In contrast, 150 nM SEQ ID NO:6 resulted in nearly complete degradation of PKR mRNA.

This result was duplicated in vivo when 2 µM SEQ ID NO:6 and the same amount of SEQ ID NO:7 were added to separate cultures of HeLa cells. These cells were incubated for 4 hours with one of the respective chimeras. As a result, PKR RNA was degraded by SEQ ID NO:6 as determined in an RT-PCR (Reverse Transcription-coupled Polymerase Chain Reaction) assay for such RNA, while apparently normal levels of PKR RNA were found in the cells treated with SEQ ID NO:7.

In addition, p(A2'p)$_3$A-antiHIV, comprising an irrelevant oligonucleotide sequence joined to 2-5A, was only weakly active in vitro and was inactive in vivo. When 50 nM, 150 nM, and 500 nM of this chimera were incubated in vitro in the presence of 100 nM PKR RNA and 2-5A-dependent RNase, substantial ribonuclease activity was observed only at the 500 nM concentration. These results further demonstrate the need for complementarity between the antisense moiety of the chimeric molecules used in the present methods and the target RNA molecule.

4. 2-5A Must be Attached to the Antisense Strand

Targeting of a molecule of RNA for cleavage by a ribonuclease has as well been found to be necessary for the specific cleavage of that molecule of RNA. When TAR:$A_{25}$:vif RNA was incubated in the Daudi extract described in Example 5 with (2'-5')$pA_4$ plus unlinked $dT_{20}$, the specific cleavage product was not produced. Another experiment involving PKR RNA as the target RNA molecule further supported these findings. In this experiment, 100 nM PKR RNA was incubated for 30 minutes at 37° C. in the presence of recombinant 2-5A-dependent RNase with either SEQ ID NO:6, a 2-5A:AS molecule containing an antisense oligonucleotide moiety exactly complementary to a part of the PKR RNA molecule, or SEQ ID NO:5, which contained the antisense oligonucleotide portion of SEQ ID NO:6 alone. SEQ ID NO:5, the antisense molecule without 2-5A attached, did not appear to induce the cleavage of the PKR RNA. Thus, 2-5A or another activator of 2-5A-dependent RNase must be attached to the antisense moiety of the chimeric molecules of the present invention in order to induce the specific cleavage of a target RNA molecule.

5. 2-5A Must be Phosphorylated, 2'5'-Linked, Trimeric, and Contain Ribose

It has been found that the 2-5A moiety of the 2-5A:AS chimeric molecule used in the present methods must be phosphorylated, 2',5'-linked, at least trimeric, and must contain ribose in order to produce the cleavage of a target RNA molecule. These characteristics are necessary for the activation of 2-5A-dependent RNase. In in vitro assays containing 100 nM PKR RNA conducted for 30 minutes at 37° C., 150 nM concentrations of chimeras containing deoxyadenosine tetramers in 3',5'-linkages (SEQ ID NO:8) had no effect on PKR RNA levels. Under the same assay conditions, chimeras having a dimeric 2',5'-adenylate molecule (SEQ ID NO:9) failed to completely induce the cleavage of PKR RNA. Chimeras having 2-5A groups whose 5' ends are not phosphorylated (SEQ ID NO:10) were likewise unable to specifically cleave such PKR RNA. Thus, these characteristics of the 2-5A moiety in the 2-5A:AS molecules used in the methods of the present invention must be satisfied when the RNase to be activated is 2-5A-dependent RNase.

E. Factors which do not Influence the 2-5A:AS Reaction

The presence or absence of linkers has not been found to significantly affect the effectiveness of the 2-5A:AS chimeric molecules used in the methods of the present invention. A linkerless form of 2-5A-antisense (SEQ ID NO:11) was synthesized and analyzed in order to determine its activity. In one experiment, 200 nM each of SEQ ID NO:6 and linkerless SEQ ID NO:11 were incubated in separate reaction mixtures with 2-5A-dependent RNase for 30 minutes at 37° C. SEQ ID NO:11 was found to be nearly as active as the linker-containing derivative SEQ ID NO:6.

III. Chimeric Molecule Analogs

A. 5'-Thiophosphate Analogs

As discussed above, our research on 2-5A:AS chimeras has established that the 5'-monophosphate moiety at the 5'-terminus of the 2-5A domain is required to effect the degradation of the targeted RNA molecule as well as for the activation of human 2-5A-dependent RNase. Earlier work (Johnston, M. and Torrence, P., *Interferon* 3:189–298 (1984)) had established that 5'-phosphorylation of 2-5A itself was needed for effective 2-5A-dependent RNase activation. A 2-5A core, bearing a free 5'-hydroxyl group, is virtually without 2-5A-dependent RNase binding and activation abilities.

Since phosphatases and related nucleotidases are of widespread occurrence in natural systems and are responsible for the dephosphorylation of nucleotide 5'-monophosphates to nucleosides (Voet and Voet, *Biochemistry*, 741–768 (1990)), the 2-5A:AS chimeric molecules used in the methods of the present invention might be subject to enzymatic dephosphorylation by such enzymes and thereby become inactivated in some in vacuo applications of the present methods. Chimeric molecules would of course also become inactivated if phosphatases and nucleotidases were present in an in vitro assay.

Extensive studies (Eckstein, F., *Angew. Chem.*, int. ed, 14:160–166 (1975); Eckstein, F., *Accounts Chem. Res.*, 12:204–210 (1979); Eckstein, F., *Angew, Chem.*, int. ed., 22:423–439 (1983)) have documented that nucleoside thiophosphates (nucleoside phosphorothioates), such as adenosine 5'-O-thiophosphate (AMPS), are extremely resistant to the action of such dephosphorylating enzymes. For instance, AMPS was degraded about 2000 times slower than AMP by alkaline phosphatase from calf intestine or *E. coli* (Eckstein, 1975), and was dethiophosphorylated much slower than AMP by nucleotidase from Crotalus. We therefore synthesized 2',5'-oligonucleotide 5'-thiophosphates in order to determine whether such compounds could activate 2-5A-dependent RNase and also be protected from dephosphorylation.

Some studies (see Sobol et al., *Nucleic Acids Res.*, 21:2437–2443 (1993)) have been conducted with the internucleotide phosphorothioate congeners to enhance resistance to phosphodiesterase degradation. Until the present invention, however, the 5'-thiophosphorylated oligonucleotides have not been reported. We have found that such chimeric molecules indeed exhibit enhanced resistance to metabolic deactivation through dephosphorylation and also are able to activate 2-5A-dependent RNase. Therefore, 5'-thiophosphorylated 2-5A:AS molecules are useful in the methods of the present invention.

In order to test the protective effects of 5'-thiophosphorylation, the trimer Sp5'A2'p5'A2'p5'A ("SPA$_3$") was constructed, where S denotes a sulfur moiety. This trimer was tested for its ability to activate 2-5A-dependent RNase in an assay which made use of a recombinant human 2-5A-dependent RNase (obtained from Dr. Robert H. Silverman, The Cleveland Clinic Foundation, Cleveland, Ohio). The effects of novel modifications of 2-5A were determined using radiolabeled poly(U) as substrate, and the percentage of the starting RNA remaining in the assay at various oligonucleotide concentrations was determined by measuring radioactivity in the acid-precipitable fraction as described by Silverman, R. H., *Anal. Biochem.*, 144:450 (1985).

Figure 10:
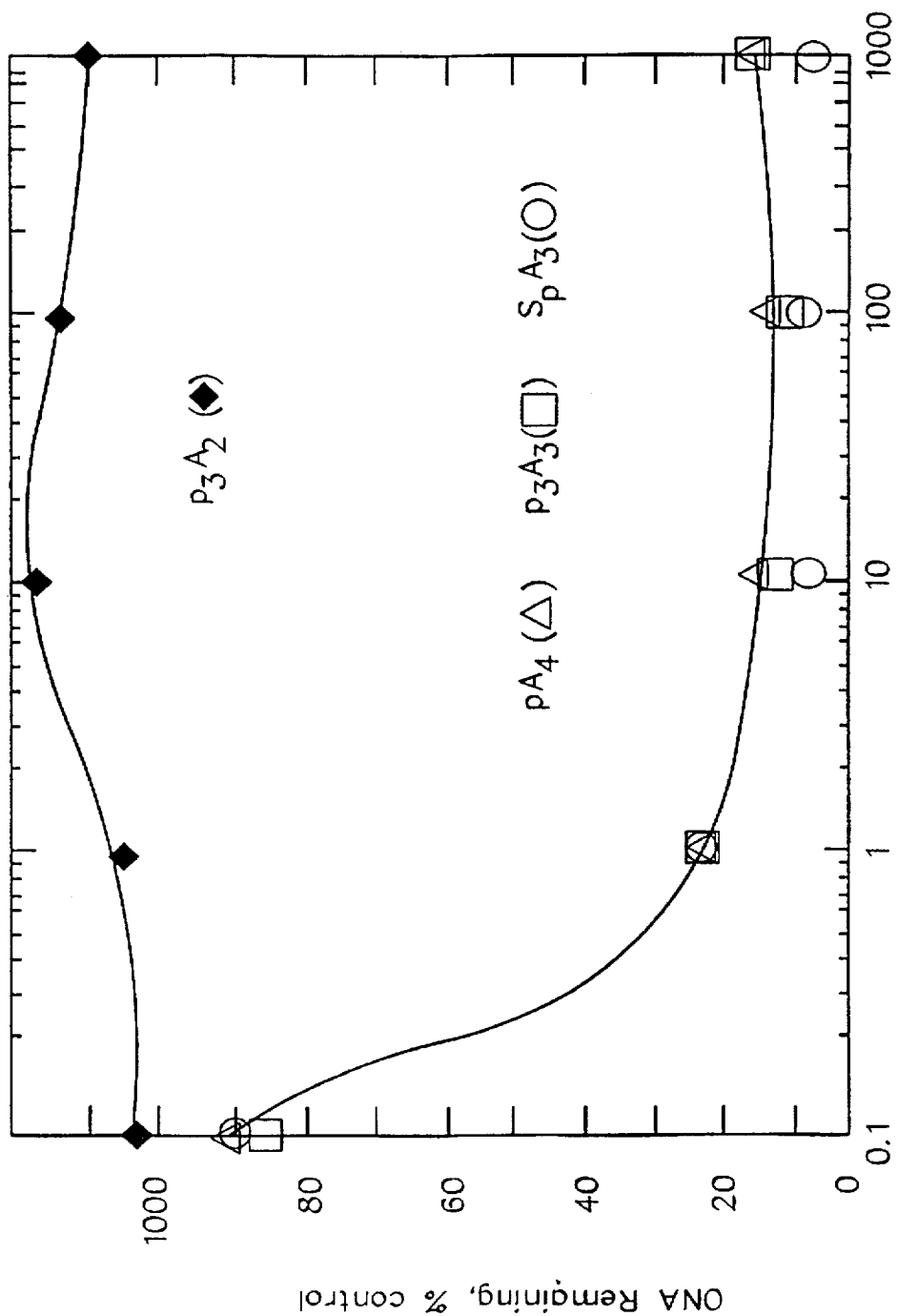
FIG. 10 is a graph showing that the 5'-thiophosphate analog of 2-5A is as active as unmodified 2-5A in its ability to activate purified, recombinant human 2-5A-dependent RNase. Assays were performed with radiolabeled poly(U) as a substrate.
Figure 11:
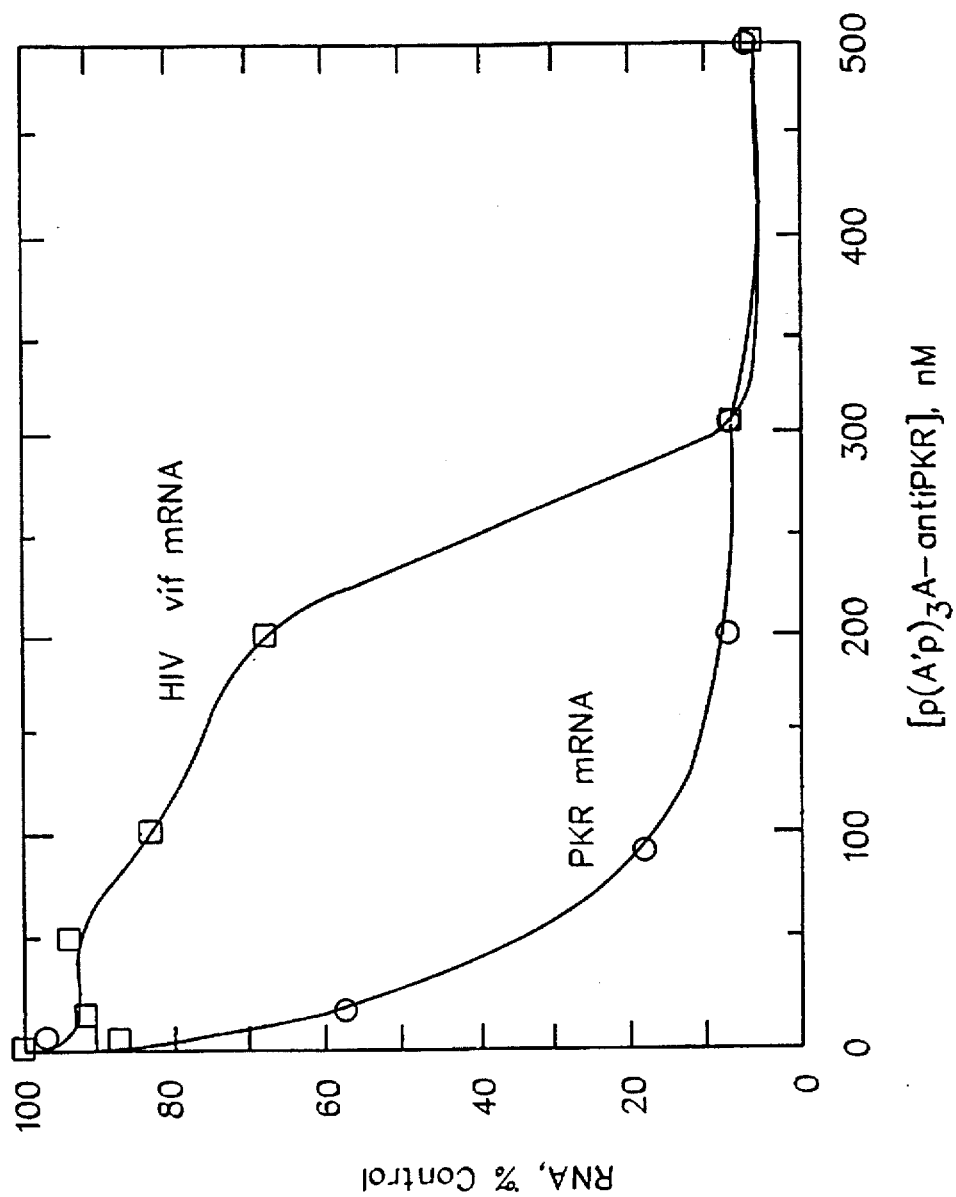
FIG. 11 is a graph showing the selectivity of 2-5A-antisense for cleaving sense strands of RNA. Data was obtained by PhosphorImager Analysis of an autoradiogrammed gel.

As shown in FIG. 10, the 5'-thiophosphate analog of 2-5A, SpA$_3$, was equally active compared to the unmodified 2-5A species, 2',5'pA$_4$ and 2',5'p3A$_3$. Therefore, the 5'-thiophosphate-containing 2-5A is a fully active 2-5A molecule. As a control, the dimer 2-5A species, p$_3$A$_2$, was used in the foregoing assay, but was found to be completely ineffective in activating 2-5A-dependent RNase to cleave RNA.

In order to determine that a 2-5A:AS molecule would still be active if the 2-5A moiety was thiophosphorylated, a 5'-thiophosphate 2-5A:AS molecule, SEQ ID NO:20, was administered to intact cells. The antisense oligonucleotide moiety of SEQ ID NO:20 is the same as that of SEQ ID NO:6. In this assay, SEQ ID NO:20 and SEQ ID NO:6 at 2 µM each were administered to HeLa cells in different microtiter wells, and these cells were incubated for 4 hours. A control well containing HeLa cells but no added oligonucleotides was also incubated. PCR amplification was then used to detect levels of PKR in these cells, as described elsewhere herein. While PKR RNA was detected in the control cells, no PKR RNA was detected in the cells treated with either SEQ ID NO:6 or SEQ ID NO:20, even after 40 cycles of PCR amplification. The 5'-thiophosphorylated 2-5A:AS chimeric molecule was therefore able to direct the specific cleavage of a target RNA molecule, in this case PKR RNA, as effectively as a similar 2-5A:AS molecule which had not been so 5'-thiophosphorylated. Thus, 2-5A:AS molecules can be made more resistant to phosphatases present in serum and in cells by conversion to 5'-thiophosphate derivatives of 2-5A:AS, and these derivatives can be used effectively in the methods of the present invention.

In order to synthesize a 5'-thiophosphorylated 2-5A:AS molecule, a DNA synthesizer can be used. The 2',5'-trimer core of such a molecule can be prepared using a Applied Biosystems 391 DNA synthesizer. The solid phase support is a column (1 cm, American Bionetics Inc.) loaded with 1.0 mole of CPG-bound N$^6$-benzoyl-5'-dimethoxytrityl-2'(3')-O-acetyladenosine (linkage to CPG via a 2'(3')-succinate) (source: Glen Research). For chain extension, N$^6$-phenoxyacetyl-5'-dimethoxytrityl-3'-O-t-butyldimethylsilyladenosine-2'-O-N,N-diisopropyl-cyanoethylphosphoramidite (Chemgenes Corporation, Waltham, Mass.) is employed. The DNA synthesizer coupling wait time is increased to 600 seconds. Under these conditions, the average coupling efficiency is about 93% as determined by spectrophotometrically quantitating the release of the dimethoxytrityl cation. The oligonucleotide is synthesized in the trityl off mode, and the resulting 5'-hydroxyl unprotected trimer is 5'-phosphorylated using: 2-[2-(4,4'-dimethoxy-trityloxy)ethylsulfonyl]ethyl-2-cyanoethyl)-(N,N-diisopropyl)-phosphoramidite (Glen Research, Sterling, Va.) at a concentration of 0.2M in anhydrous tetrazole/acetonitrile (Applied Biosystems). Sulfurization is accomplished with 3H-1,2-benzodithiole-3-one 1,1-dioxide (Lyer et al., *J. Am. Chem. Soc.*, 112:1253–1254 (1990)) in anhydrous acetonitrile.

The synthesized oligomer is cleaved from the solid support with concentrated NH$_4$OH/EtOH (3:1) treatment for 2 hours at room temperature. The temperature then is increased to 55° C. and incubation is continued for 8 hours to remove N-benzoyl groups. Finally, the t-butyldimethylsilyl protecting groups are removed by treatment with 1 mL of 1 M tetrabutylammonium fluoride in THF at room temperature overnight.

The above-produced crude deprotected product first is desalted on a C-18 SEP-PAK cartridge (from Waters Associates) and then is HPLC (High Performance Liquid Chromatography) purified on an Ultrasphere semiprep ODS column, using Beckman 110B solvent delivery modules controlled by an NEC computer with detection at 260 nm (Knauer variable wavelength monitor). The elution program is 0–50% solvent B in solvent A over 30 minutes where solvent A is 50 mM ammonium acetate (pH 7.0) and solvent B is MeOH/H$_2$O (1:1, v/v). The combined oligonucleotide containing eluate is concentrated and desalted by application to a DEAE-Sephadex A-25 column and subsequent elution with a gradient of 0.1–0.8M triethylammonium bicarbonate, pH 7.5 (TEAB). Oligonucleotide-containing fractions are combined, the water evaporated, and then several additions and evaporations of water are carried out in order to remove all residual TEAB. Finally, the product is dissolved in H$_2$O and applied to a column of Dowex 50W x8 cation exchange resin (Na+ form) to convert the oligonucleotide to its sodium salt (26 A$_{260}$ units).

A snake venom phosphodiesterase digestion is next carried out in order to characterize the oligonucleotides resulting from the above synthesis. The oligonucleotide (0.2 A$_{260}$) is digested with snake venom phosphodiesterase (*Crotalus adamantus*, Pharmacia/P. L. Biochemicals Inc, Piscataway, N.J.) in a buffer of 50 mM Tris HCl, 0.5 mM MgCl$_2$, pH 7.8, for 1 hour at 37° C. The products of the digestion are analyzed by HPLC on an Ultrasphere ODS column at a flow rate of 0.5 mL/min using an isocratic elution program of 5% Solvent B in solvent A where A is 100 mM ammonium phosphate, pH 7.0, and B is MeOH/H$_2$O (1:1, v/v). Under these conditions, the synthetic product yielded 5'AMP and AMPS in a ratio of 2:1, thereby corroborating the assigned structure, Sp5'A2'p5'A2'p5'A. [$^1$H-NMR (D$_2$O) δ (ppm): 5.7–6.2 (3d, J=2.56, 3.39, 4.18 Hz, 3×1H, 3 H1'); 7.7–8.4 (6s, 6H, purine H-2 & H-8). $^{31}$P-NMR (D$_2$O) δ (ppm): –0.8 & –0.6 (2, internucleotide phosphate P); 42.0 (1P, 5'-thiophosphate P).]

EXAMPLE 8

Synthesis of a 5'-Thiophosphorylated 2-5A:AS Chimera

The procedure for the synthesis of the 5'-thiophosphorylated analog Sp5'A2'p5'A2'pA2,p5'Ap(CH$_2$)$_4$p(CH$_2$)$_4$p5'pGTA CTA CTC CCT GCT TCT G3' (SEQ ID NO:20) is essentially identical to that described in Example 1 and elsewhere for the synthesis of other 5'-phosphorylated chimeric molecules, except for the thiophosphorylation step which was performed as described above.

The crude product was desalted on a C18 SEP-PAK and then purified by HPLC using a Nucleogen DEAE 60-7 column (4×125 mm). The elution program was 10–80% buffer B in buffer A where buffer A was 20% acetonitrile in 50 mM ammonium phosphate (pH 7.0) and buffer B was 1M KCl in 50 mM potassium phosphate (pH 7.0). The flowrate was 1 mL/min. After desalting on a Sephadex G-25M column, a total of 24 A$_{260}$ units of oligonucleotide (uv lmax=261 nm) were obtained. Capillary electrophoresis (microgel column, 75 mM Tris phosphate buffer (pH 7.6) containing 10% MeOH, run at –12 kV (15 A) showed the presence of only a single peak.

Structure confirmation was obtained through snake venom phosphodiesterase (Pharmacia/P-L Biochemicals) digestion under the usual conditions followed by analysis by HPLC. An Ultrasphere ODS column (0.46×25 cm) was used at a flowrate of 0.5 mL/min. Two different elution programs were employed for analysis of the results of the digestion. Program A was 5% solvent B in solvent A for 20 min followed by 5–55% solvent B in solvent A for 18 min where solvent A was 100 mM ammonium phosphate (pH 7.0) and solvent B was MeOH/H$_2$O (1:1, v/v). Program B was 3–5% solvent B in solvent A for 20 min followed by 5–55% solvent B in solvent A for 18 min where solvent A was 100 mM ammonium phosphate (pH 5.5) and solvent B was MeOH/H2O (1:1, v/v). Analysis using elution program A (which did not separate AMP & TMP) revealed a molar ratio of dCMP/dGMP/dAMP/AMPS/(AMP & TMP)/A$_{linker}$ of 7:3:2:1:9:1. Using program B, the molar ratio of dCMp/dGMP/dAMP/TMP/AMPS/AMP/A$_{linker}$ was 7:3:2:7:1:2:1.

B. Tailed Chimeric Molecule Analogs

Earlier studies have shown that the addition of any of a variety of chemical modifications at the 3' (or 2') terminus of an oligonucleotide can stabilize it against degradative enzymes, especially phosphodiesterases (Imai et al, *J. Biol. Chem.*, 257:12739–12745 (1982); Clarenc et al., 8:81–94 (1993); Herdewijn et al., *Helv. Chem. Acta*, 74:7–231991 (1991); Petrie et al., *Bioconjugate Chem.*, 3:85–87 (1992); Baglioni et al, *J. Biol. Chem.*, 256:3253–3257 (1981); also see Alster et al, *Biochem. Biophys. Res Commun.*, 141:555–561 (1986) and references cited therein). For this reason, we prepared SEQ ID NO:21, a 3'-modified analog of SEQ ID NO:6, to determine the effect of such a chemical change on the biological activity of a 2-5A:AS chimeric molecule.

SEQ ID NO:21 has a C3 alkylamine moiety at the 3' end of the antisense oligonucleotide moiety of the 2-5A:AS molecule. The structure of this C3 alkylamine moiety is shown below, with the underlined OH moiety indicating the location of a phosphodiester linkage which connects the C3 alkylamine moiety to 3' end of the antisense oligonucleotide:

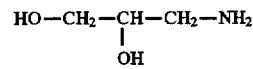

The addition of a moiety such as the foregoing to the 3'-terminus of an oligonucleotide has been referred to as "tailing" (Imai et al, 1982).

In an in vivo assay, 2 µM SEQ ID NO:21 was able to cleave PKR RNA in HeLa cells as well as SEQ ID NO:6 and SEQ ID NO:20 (the 5'-thiophosphate analog of SEQ ID NO:6). After 40 rounds of PCR, no PKR RNA was detected in such cells after a 4 hour incubation. Therefore, the 3' modification of SEQ ID NO:21 may make it more bioactive, either through increased cell permeability and stability or through some other mechanism of action. Therefore, "3'-tailed" chimeric molecules, especially molecules carrying 3'-alkyl amine moieties, are perceived as being of use in vivo applications of the methods of the present invention. In a preferred embodiment, the chimeric molecules used in the methods of the present invention can be 5'-thiophosphorylated and 3'-tailed, thus achieving the advantages conferred by each of the 5'-thiophosphorylate and 3'-tail moieties.

EXAMPLE 9

Synthesis of a Tailed 2-5A:AS Chimeric Molecule

The synthesis of SEQ ID NO:21 began with a modified solid support; namely, the Amine-ON C3 CPG column (Clontech, Palo Alto, Calif.). This was used as the support for the addition of the p5'A2'p5'A2'pA2'p5'Ap(CH$_2$)$_4$P(CH$_2$)$_4$p5'pGTA CTA CTC CCT GCT TCT G3' sequence, which was produced using Applied Biosystems DNA synthesizer according to the methodology previously described herein. The product oligonucleotide was cleaved from the column and deprotected also in the usual way and then desalted on a C-18 SEP-PAK cartridge. Final purification was on a Nucleogen DEAE 60-7 ion exchange column (4×125 mm) using a flowrate of 1 mL/minute. The elution program was a linear gradient of 10–18% buffer B in buffer A over 30 minutes, where buffer A was 20% acetonitrile in 50 mM potassium phosphate (pH 7.0) and buffer B was 1 M KCl in 50 mM potassium phosphate (pH 7.0). The eluted product was desalted on a Sephadex G-25M column (Pharmacia/P-L Biochemicals). The yield was 26 A$_{260}$ units. The product showed only one peak when subjected to capillary electrophoresis.

Characterization and structure confirmation was supplied through snake venom phosphodiesterase digestion under the aforedescribed conditions. Digestion product analysis was carried out on an Ultrasphere ODS column at a flowrate of 0.5 mL/min using a linear gradient of 3–5% buffer B in buffer A over 20 min, and then 5–55% buffer B in buffer A in 18 min where buffer A was 100 mM ammonium phosphate (pH 5.5) and buffer B was MeOH/H$_2$O. From this digestion, seven products are obtained: dCMP, dGMP, dAMP, TMP, AMP, adenosine coupled to the linkers (A$_{linker}$), and dGMP coupled to the 3' C3 amine in a ratio of 7:7:2:3:2:1:1. The structure of the latter product was confirmed through a separate synthesis by reaction of the C3 Amine ON CPG with the protected dG phosphoramidite normally used in the DNA synthesis. In other words, dG only was added to the C3 CPG support, whereas cleavage, deprotection and purification were performed as described elsewhere. This product gave an identical retention time to a peak obtained from the snake venom digested oligonucleotide. In addition, it gave the expected molecular ion (501, M+1) obtained by mass spectroscopy.

IV. In Vivo Effect of 2-5A:AS Chimeric Molecules

One of the surprising findings of the present invention is that 2-5A:AS chimeric molecules can be administered to mammalian cells and can effect the targeted destruction of a particular molecule of RNA without having to treat such cells in any special way in order to pass the chimeric molecules into the cells. This finding is contrary to the teachings of the prior art, which has had to result to harsh cell treatments in order to pass antisense oligonucleotides into cells. The present invention therefore represents an important advance in the use of antisense oligonucleotides in vivo.

In order to determine that 2-5A:AS molecules are able cleave target RNA molecules in cells, 2-5A:AS molecules targeting PKR RNA (including SEQ ID NO:6, SEQ ID NO:20, and SEQ ID NO:21) at 2 µM were added to HeLa cell cultures in microtiter wells. After four hours of incubation at 37° C., the total RNA was isolated from the cells in each well using RNazol reagent by methods known to those of Skill in the art. A control well to which no chimeric molecule was added was also incubated, and the mRNA from the cells of that well was also isolated.

PKR mRNA contained in the cells treated as above was detected using a reverse transcription-coupled PCR method (RT-PCR). First, the mRNA was reverse transcribed into cDNA using oligo(dT) as primer; then the cDNA was diluted three times at 1:4, and the PKR DNA in each dilution was amplified using primers to antisense and sense orientation sequences at opposite ends of the PKR coding sequence. To detect the amplified PKR DNA, it was blotted to Nytran membrane and then probed with radiolabeled PKR cDNA. In control cells to which no oligonucleotides were added, the signal increased in proportion to the number of PCR cycles, and it decreased upon dilution of the cDNA. In contrast, there was no PKR mRNA detected after incubations of the cells With SEQ ID NO:20, SEQ ID NO:21, or SEQ ID NO: 6. Therefore, these three species of 2-5A-antisense caused the ablation or apparent cleavage of all of the intact PKR mRNA in the HeLa cells.

In contrast, 5'-phosphorylated and 5'-unphosphorylated antisense oligonucleotide molecules which had the same sequences as the antisense oligonucleotide moiety of SEQ ID NO:6 (i.e., SEQ ID NO:4 and SEQ ID NO:5) did not induce the cleavage of PKR mRNA in these HeLa Cells. Chimeric molecules carrying sequences not complementary to PKR RNA, such as p(A2'p)$_3$A-antiHIV, also did not effect such cleavage. SEQ ID NO:19, p(A2'p)$_3$A-dA$_{18}$, similarly had no effect on PKR mRNA levels. These results show that 2-5A:AS requires the 2-5A moiety, and also indicate that the antisense oligonucleotide moiety of the chimeric molecule must be complementary to the target mRNA for RNA degradation to occur.

To determine if the 2-5A:AS molecule was specific in its mechanism of action, levels of β Actin mRNA were also measured by the same method. Of the antisense oligonucleotides or chimeric molecules tested, including SEQ ID NO:4, SEQ ID NO:6, SEQ ID NO:19, SEQ ID NO:20, SEQ ID NO:21, and 2-5A-antiHIV, none appeared to affect the levels of β Actin mRNA in the cells. Therefore, 2-5A:AS does not damage mRNA which is not being targeted.

Several additional controls were performed to demonstrate the mechanism of action. It was found that the addition to the cells of chimeric molecules containing the PKR sense orientation sequence SEQ ID NO:7 was without affect on PKR mRNA levels. Replacement of the 2-5A group with the 3',5'-deoxyoligoadenylate p(dA3'p)$_3$dA (SEQ ID NO:8) also failed to produce cleavage of PKR mRNA in the HeLa cells. Removal of the 5'-phosphoryl group from the 2-5A:AS molecule (SEQ ID NO:10) inactivated it as well. Also, a 2-5A:AS molecule carrying only a 2-5A dimer (SEQ ID NO:9), was inactive, as was SEQ ID NO:14, in which ten mismatches were introduced into the antisense sequence. Therefore, to induce RNA cleavage in intact cells, 2-5A which can activate 2-5A-dependent RNase must be present in the 2-5A:AS molecule and complementarity between the antisense moiety of the chimeric molecule and the target sequence must be maintained.

To confirm the ablation of PKR mRNA using an independent and quantitative method, an RNase protection assay was performed. An antisense probe was prepared from BamHI digested pGEM-8 plasmid containing PKR cDNA sequence from nucleotides 1 to 383 (where 1 denotes the first nucleotide of the coding sequence). A radiolabeled fragment of antisense RNA to PKR was synthesized using SP6 RNA polymerase. Separately, HeLa cells were incubated with 2 µM of either 2-5A-anti PKR (SEQ ID NO:6) or 2-5A-sensePKR (SEQ ID NO:7) for 4 hours. The labeled probe was hybridized at 45° C. for 16 hours to RNA isolated from the HeLa cells so incubated. After hybridization, the RNA was digested with RNases A and T1 for 30 minutes at 30° C. followed by proteinase K treatment at 37° C. for 15 minutes. The RNA products were then purified by phenol extraction and were applied to a 6% polyacrylamide-urea gel. The results show that SEQ ID NO:6 caused the ablation of PKR mRNA while SEQ ID NO:7 was without effect.

Levels of the PKR protein per se were also greatly reduced in the HeLa cells treated with SEQ ID NO:6. In further experiments, levels of the PKR protein were determined on Western blots using monoclonal antibody to PKR and the ECL (enhanced chemiluminesence) method (Amersham). Treatment of HeLa cells for 16 hours with three forms of 2-5A:AS targeting PKR RNA (SEQ ID NO:6, SEQ ID NO:20, and SEQ ID NO:21), each at 2 µM, all greatly reduced PKR protein levels. Anti-PKR antisense oligonucleotides (SEQ ID NO:4) resulted in a lesser reduction in PKR levels. In a separate experiment, treating HeLa cells with SEQ ID NO:6 (2 µM) twice daily for 3.5 days greatly reduced PKR levels while PKR antisense oligonucleotides alone (SEQ ID NO:4) and p(A2'p)$_3$A-antiHIV were without affect. These results demonstrate that both RNA and protein levels are downregulated by 2-5A:AS in intact cells.

Cycloheximide-inhibition of PKR synthesis was performed to demonstrate that PKR is a relatively stable (long-lived) protein. In tests to induce PKR protein production, a several fold increase in PKR levels was obtained by treating cells with poly(I):poly(C) at 100 µg per ml for 16 hours. When SEQ ID NO:6 at 1 µM was added to HeLa cells together with the poly(I):poly(C), SEQ ID NO:6 completely prevented poly(I):poly(C) induction of PKR. In contrast, the same antisense oligonucleotide species lacking the 2-5A moiety (i.e., SEQ ID NO:4) only very slightly inhibited PKR induction by poly(I):poly(C).

These results are significant in that they show that 2-5A greatly enhances the ability of an antisense oligonucleotide to inhibit specific gene expression. Furthermore, these findings also show that the methods of the present invention are effective against a natural mRNA species in intact cells. Significantly, no special techniques were required for introducing the oligonucleotides into the cells. The oligonucleotides and chimeric molecules used in the foregoing experiments were simply added to existing cell cultures.

Figure 9:
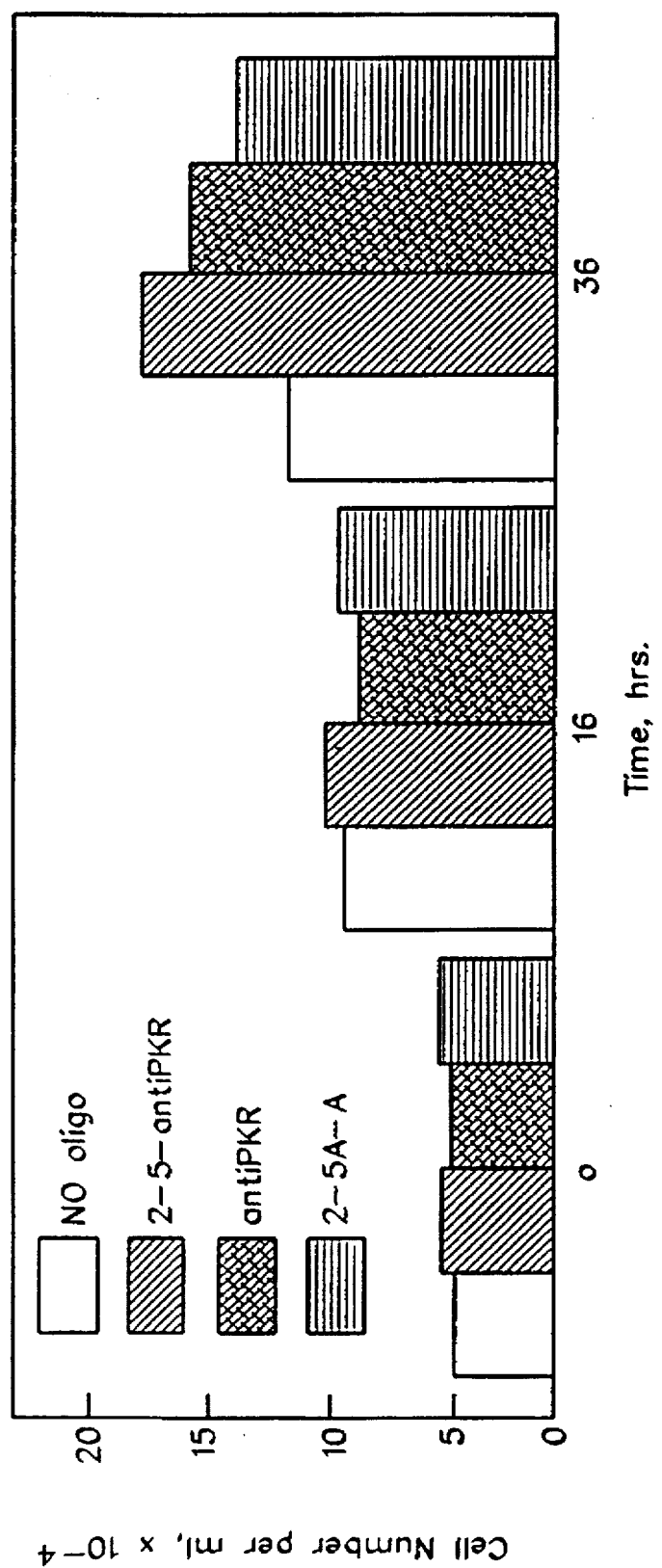
FIG. 9 is a bar graph illustrating that 2-5A-antisense at 2 μM is not toxic to HeLa cells. Viable cell numbers Were determined by trypan blue dye exclusion assay in a hemocytometer.

To determine whether 2-5A:AS is inhibitory to cell growth, we measured live cells cultured in the presence of SEQ ID NO:6. Viable cell numbers were determined in the presence of trypan blue dye in a hemocytometer. Neither p(A2'p)$_3$A-antiPKR (SEQ ID NO:6) nor p(A2'p)$_3$A-dA18 (SEQ ID NO:19), both at 2 µM, were inhibitory to cell proliferation (see FIG. 9). AntiPKR oligonucleotides (SEQ ID NO:4) also lacked any cytotoxicity in this assay. Therefore, 2-5A:AS at 2 µM induces targeted cleavage of mRNA without cytotoxicity.

V. Therapeutic Treatment of Subjects with Chimeric Molecules

The present methods of specifically cleaving a fragment of RNA in an intact, untreated cell can be used therapeutically to treat subjects whose cells contain 2-5A-dependent RNase. 2-5A-dependent RNase has been found in species ranging from reptiles to birds to mammals, including humans. Therefore, any of these groups of species, as well as any others whose cells contain 2-5A-dependent RNase, can be treated according to the present methods.

Many medical conditions are produced by mechanisms which involve RNA, particularly mRNA, as at least an intermediate step in such mechanisms. Such conditions are therefore susceptible to treatment according to the present methods. For example, if a subject is suffering from a viral infection, a 2-5A:AS molecule can be administered to that subject to treat the infection. The RNA coding for a viral protein that is necessary for viral replication or infectivity, for example, can be targeted by the molecule of 2-5A:AS in order to inhibit the expression of that protein. Any number of viral infections can be treated in this way, including HIV infections (which lead to AIDS), Papilloma virus infections (which cause warts), and Herpes infections. As an example of this, a 2-5A:AS molecule whose antisense oligonucleotide moiety is complementary to the gag or rev mRNA's of the HIV virus can be administered to a subject infected with HIV in order to inhibit viral replication (See, e.g., Lisziewicz, J. et al., *Proc. Natl. Acad. Sci. USA*, 90:3860–3864 (1993)).

In order to cleave a molecule of RNA coding for a viral protein which is essential for a virus' replication a 2-5A:AS molecule whose antisense moiety is complementary to an RNA transcript of the virus which codes for a viral protein that is essential for the virus' replication is first administered to a subject carrying the virus. The 2-5A:AS molecule is then taken into cells infected with the virus, where it targets the cleavage of the viral RNA transcript with which it is complementary. Once the viral RNA transcript is cleaved, the viral protein for which it codes will not be translated or will be translated only partially, thus effectively inhibiting or stopping the replication of the virus. Alternatively, if the virus is a single stranded RNA virus, the antisense moiety of the 2-5A:AS molecule can be targeted against a sequence in the viral genome itself.

Other medical conditions can also be treated with chimeric molecules according to the methods of the present invention. For example, a person suffering from cancer can be treated in order to stop the overproduction of an oncogene. A person having a cancer related to the overproduction of the oncogene c-myc can be treated by administering to that person a solution containing molecules of 2-5A:AS whose antisense oligonucleotide moieties are complementary to c-myc RNA. The cells containing this oncogene will take up the chimeric molecule, and the chimeric molecule will then hybridize with the c-myc mRNA in such cells, thereby effecting the specific cleavage of these mRNA molecules. The cleavage of the c-myc mRNA prevents its full translation into the corresponding protein, thereby preventing the disease manifestation. Other cancers, such as leukemia, can also be treated, such as with a 2-5A:AS molecule targeting the mRNA product of the BCR-ABL gene (See, e.g., Szczylik, C. et al., *Science*, 253:562 et seq. (1991)).

In addition, cardiovascular conditions such as restenosis can be treated according to the present methods. After vascular angioplasty, which is performed to unclog blood vessels, the treated blood vessels sometimes become narrowed again due to the proliferation of cell wall tissue at the site of the angioplasty procedure. In order to treat or prevent such smooth muscle cell proliferation, a chimeric molecule can be administered to a subject who has undergone angioplasty. For example, a molecule of 2-5A:AS whose antisense oligonucleotide moiety is complementary to the mRNA transcribed from the proto-oncogene c-myb can be administered either intravenously or by direct infusion through an angioplasty catheter being used to perform an angioplasty procedure (see Simons, M. et al., *Nature*, 359:67 et seq. (1992)). Since the c-myb RNA is involved in mediating cell wall smooth muscle cell proliferation, the targeted cleavage of this RNA by 2-5A:AS will result in the inhibition of such proliferation and the prevention or amelioration of restenosis.

Because 2-5A-dependent RNase is believed to be present in most mammalian cells, the therapeutic control of protein translation for the treatment of cancer, viral infections, genetic diseases, osteoarthritis, rheumatoid arthritis, restenosis, and a variety of other medical conditions can be accomplished using this technology. Other therapeutic applications employing 2-5A:AS chimeric molecules are also contemplated. For example, chimeric molecules can be used to modulate the immune response (see Mojcik, C. F. et al., *Clin. Immun. Immunopath.* 67:130–136 (1993)), to modulate behaviour (see Hinrichsen, et al., *Proc. Natl. Acad. Sci. USA*, 89:8601–8605 (1992)), to control foot-and-mouth disease in animals (see Polatnick, J. and Wool, S., *J. Virol.*, 40:881–889 (1981)), and to treat parasitic diseases in animals or humans (see Cornelissen, A., et al., *Nucleic Acids Res.*, 14:5605–5614 (1986)). In general, any condition which is brought on due to the translation of a protein can be treated with chimeric molecules according to the methods of the present invention by cleaving the mRNA molecule which codes for that protein.

When administering a molecule of 2-5A:AS therapeutically, the antisense oligonucleotide moiety of the chimeric molecule is preferably chosen so as not to cleave a non-targeted RNA molecule in the cells of a treated subject. In order to thus select a chimeric molecule, the antisense oligonucleotide moiety of the molecule is preferably checked against a library of known RNA and/or DNA sequences, such as GertBank or EMBL. A program such as the Blast computer program can be used to search these nucleotide sequence data banks (searching tools and techniques are discussed, for example, in Altschul, S. F. et al., "Basic local alignment search tool," *J. Mol. Biol.*, 215:403–410 (1990)). If it is discovered that an RNA sequence exists in the subject which is not being targeted but which is complementary to a chimeric molecule being administered, then an alternate antisense oligonucleotide moiety is preferably chosen for the chimeric molecule. If the discovered RNA sequence is part of an RNA molecule that codes for a stable protein in the subject or which codes for a protein whose expression can be temporarily interrupted without harming the subject, however, chimeric molecules complementary to such discovered RNA sequences can still be administered to the subject according to the present methods, since such administration will not be likely to harm the subject.

Chimeric molecules can be administered to a subject either through direct application or through infusion into the tissue affected by the medical condition or through systemic administration such as intravenous injection. When administering chimeric molecules topically through direct application to a tissue, the chimeric molecule applied can be placed in aqueous solution, lotion, jelly, or other topical carrier known to the art. For example, when treating Herpes simplex infections of the mucous membranes or Papilloma skin infections (i.e., warts), a topical solution of chimeric molecules such as 2-5A:AS in an aqueous carrier can be directly applied to such affected tissues. Direct application should provide a more effective route of administration for tissues which can be clinically treated in this way.

When administered through intravenous, intramuscular, iontophoresis, intraperitoneal, subcutaneous, or other systemic or direct infusion routes of administration which carry chimeric molecules into the interior of a subject's body, a chimeric molecule is preferably administered in a pharmacologically acceptable carrier, such as phosphate buffered saline, as is known to those of skill in the art. Chimeric molecules can also be administered by any other means known to the art for internally delivering pharmaceutical agents to a subject. Once chimeric molecules have been administered to a subject, they are taken up by cells and effect the cleavage of the targeted RNA molecules.

Systemic injection and direct infusion or application of chimeric molecules are preferred routes of administration. Other methods of administering the chimeric molecule can include the co-administration of agents which increase cell membrane permeability, such as lysolecithin and lipofectin. In addition, the chimeric molecule can be packaged into liposomes prior to injection into the mammalian host. Well known methods are available for packaging polynucleotide molecules into liposomes. Although such measures are not absolutely necessary in light of the finding that cells spontaneously uptake 2-5A:AS molecules without treatment, such facilitators of cellular uptake may be advantageous in certain applications in order to increase the potency of chimeric molecule treatments or to facilitate the uptake of certain chimeric molecules.

When administering 2-5A:AS molecules and other chimeric molecules according to the methods of the present invention, such molecules are preferably administered daily for the course of the treatment regimen. Depending on the condition being treated, the treatment regimen can continue for a week, two weeks, a month, two months, six months, a year, indefinitely, or until clinical symptoms are no longer detectable. Less frequent administration of chimeric molecules is also possible in accordance with the present invention. For example, if a particular mRNA molecule coding for a protein whose expression is being inhibited by a chimeric molecule is not continuously transcribed or is transcribed slowly, then a chimeric molecule composition can be administered once every two days, weekly, or as otherwise determined by a clinician.

The chimeric molecule compositions administered according to the present methods, particularly those administered systemically, preferably contain between about 0.001 mg/kg and 1,000 mg/kg of chimeric molecules, such as 2-5A:AS. More preferably, such compositions contain between about 0.1 mg/kg and 100 mg/kg, and more preferably still they contain between about 1.0 mg/kg and 10 mg/kg. These mass-based ranges will vary, of course, depending on the size of the oligonucleotide. Other parameters known to those of skill in the art will also determine which range is most useful in a particular application.

Topical and systemically administered compositions can also contain chimeric molecules at concentrations of between about 0.01 µM and 10 mM. More preferably, such compositions contain chimeric molecules concentrations of between about 0.1 µM and 100 µM, and more preferably still between about 1.0 µM and 5.0 µM.

EXAMPLE 10

Treating a Mammal Having Leukemia with a Chimeric Molecule

A human subject diagnosed as having leukemia is intravenously administered a 5 mg/kg dose of a 2-5A:AS molecule whose antisense oligonucleotide moiety is complementary to a sequence of nucleotides present in the mRNA transcript of the BCR-ABL gene. This dose is administered in a pharmacologically acceptable carrier solution, and administration is continued weekly for 6 months or until symptoms of leukemia are no longer present in the subject. The number of colony forming neoplastic cells is reduced.

EXAMPLE 11

Treating a Mammal Having a Herpes Simplex Infection with a Chimeric Molecule

Approximately 5 ml of a 5 µM aqueous solution of a 2-5A:AS molecule whose antisense oligonucleotide moiety is complementary to a sequence of nucleotides present in the mRNA transcript of a Herpes simplex structural gene is topically applied to Herpes simplex sores on the lip of a human subject. The solution is applied once daily until the sore heals.

EXAMPLE 12

Treating a Mammal Having a Herpes Infection of the Eye with a Chimeric Molecule

Approximately 5 ml of a 5 µM aqueous solution of a 2-5A:AS molecule whose antisense oligonucleotide moiety is complementary to a sequence of nucleotides present in the mRNA transcript of a Herpes simplex structural gene is topically applied to the eye of a human subject to treat a Herpes simplex infection of the subject's eye. The solution is applied once daily until the infection heals

EXAMPLE 13

Treating a Mammal Having an HIV Infection with a Chimeric Molecule

A human subject diagnosed as being infected with Human Immunodeficiency Virus is intravenously administered 5 ml of a 5.0 mM aqueous solution of a 2-5A:AS molecule whose antisense oligonucleotide moiety is complementary to a sequence of nucleotides present in the mRNA transcript of the rev gene. Administration is twice weekly indefinitely to suppress HIV replication.

EXAMPLE 14

Treating a Mammal Experiencing Restenosis with a Chimeric Molecule

A mammal which has undergone an angioplasty procedure is intravenously administered a 50 mg/kg dose of a 2-5A:AS molecule whose antisense oligonucleotide moiety is complementary to a sequence of nucleotides present in the mRNA transcript of the proto-oncogene c-myb in a pharmacologically acceptable carrier solution. Administration is performed immediately after angioplasty and then once weekly for six weeks or as needed until the smooth muscle cells at the site of the angioplasty procedure are no longer proliferating.

EXAMPLE 15

Preparation of a Chimeric Molecule Composition for Intravenous or Topical Delivery About 25 mg of SEQ ID NO:6 is dissolved in 5 ml of phosphate buffered saline (pH 6) with 50 μl DMSO.

The references cited herein are hereby incorporated by reference. In addition, the sequences of the chimeric molecules referred to herein can be found in either or both of Table 3 or the Sequence Listing below. Although the present invention has been described in terms of certain specific embodiments, the scope of the invention is not intended to be limited by such specific embodiments. For example, although the present method is described in terms of using 2-5A-dependent RNase, it is believed that other RNases exist which require an activator to enable or substantially increase the ability of such RNases to degrade RNA. Thus, it is believed that RNases which require an activator can be directed to specifically cleave a sense strand of RNA by attaching such an activator to an antisense oligonucleotide and then hybridizing that oligonucleotide to the sense strand of RNA.

Further, the sequence and nature of the antisense oligonucleotide moiety of the chimeric molecule used in the methods of the present invention is not limited to the specific examples of such moieties provided herein. Those of skill in the art will therefore appreciate that the present methods can be modified within the scope of the invention in order to make use of activators of other RNases as well as to make use of other antisense oligonucleotides. In addition, those of skill in the art will understand that alternate reagents, methods of administration, and other parameters can be used without departing from the scope of the invention. The specific embodiments detailed above are therefore meant to be illustrative only and not limiting.

TABLE 3

2-5A:AS Chimeric Molecules*

| SEQ ID NO: | | Chimeric Molecule |
|---|---|---|
| 4 | antiPKR | p5'GTA CTA CTC CCT GCT TCT G3' |
| 5 | antiPKR-core | GTA CTA CTC CCT GCT TCT G3' |
| 6 | pA$_4$-antiPKR | p5'A2'p5'A2'p5'A2'p5'A2'-C$_4$-p-C$_4$-p5' GTA CTA CTC CCT GCT TCT G3' |
| 7 | pA$_4$-sensePKR | p5'A2'p5'A2'p5'A2'p5'A2'-C$_4$-p-C$_4$-p5' CAG AAG CAG GGA GTA GTA C3' |
| 8 | 3',5'-pdA$_4$-antiPKR | p5'dA3'p5'dA3'p5'dA3'p5'dA3'-C$_4$-p-C$_4$-p5'GTA CTA CTC CCT GCT TCT G3' |
| 9 | pA$_2$-antiPKR | p5'A2'p5'A2'-C$_4$-p-C$_4$-p5'GTA CTA CTC CCT GCT TCT G3' |
| 10 | 2-5A core A$_4$-antiPKR | A2'p5'A2'p5'A2'p5'A2'-C$_4$-p-C$_4$-p5'GTA CTA CTC CCT GCT TCT G3' |
| 11 | pA$_6$-antiPKR (LINKERLESS) | p5'A2'p5'A2'p5'A2'p5'A2'p5'A2' p5'A2'p5'GTA CTA CTC CCT GCT TCT G3' |
| 12 | m$_1$-pA$_4$-antiPKR | p5'A2'p5'A2'p5'A2'p5'A2'-C$_4$-p-C$_4$-p5' GTA CTA CAC CCT GCT TCT G3' |
| 13 | m$_4$-pA$_4$-antiPKR | p5'A2'p5'A2'p5'A2'p5'A2'-C$_4$-p-C$_4$-p5' GTA CTT CAC CCA CCT TCT G3' |
| 14 | m$_{10}$-pA$_4$-antiPKR | p5'A2'p5'A2'p5'A2'p5'A2'-C$_4$-p-C$_4$-p5' CAA GTT CAC GCA CCA ACT G3' |
| 15 | nt$_{15}$-pA$_4$-antiPKR | p5'A2'p5'A2'p5'A2'p5'A2'-C$_4$-p-C$_4$-p5' CTA CTC CCT GCT TCT3' |
| 16 | nt$_{12}$-pA$_4$-antiPKR | p5'A2'p5'A2'p5'A2'p5'A2'-C$_4$-p-C$_4$-p5' CTA CTC CCT GCT3' |
| 17 | nt$_9$-pA$_4$-antiPKR | p5'A2'p5'A2'p5'A2'p5'A2'-C$_4$-p-C$_4$-p5' CTA CTC CCT3' |
| 18 | nt$_6$-pA$_4$-antiPKR | p5'A2'p5'A2'p5'A2'p5'A2'-C$_4$-p-C$_4$-p5' CTA CTC3' |
| 19 | pA$_4$-anti(dT)$_n$ | p5'A2'p5'A2'p5'A2'p5'A2'-C$_4$-p-C$_4$-p5' dA2'(p5'dA2')$_{16}$p5'dA |
| 20 | Sp(A2'p)$_3$A-antiPKR | sp5'A2'p5'A2'p5'A2'p5'A2'-C$_4$-p-C$_4$-p5 'GTA CTA CTC CCT GCT TCT G3' |
| 21 | p(A2'p)$_3$A-antiPKR-3'-C3 amine tail | p5'A2'p5'A2'p5'A2'p5'A2'-C$_4$-p-C$_4$-p5'GTA CTA CT CCT GCT TCTG3'C3 amine |

*The notation 5'GTA . . . TCT G3' is used in this table, as elsewhere herein, to denote a nucleotide sequence, with 5' and 3' denoting the 5' end and 3' end of the nucleotide sequence, respectively.

What is claimed is:

1. An improvement in a method wherein an antisense oligonucleotide complementary to a target strand of RNA is administered to a mammal to reduce or inhibit the activity of the RNA molecule in a cell of the mammal, the improvement comprising attaching an activator of 2-5A-dependent RNase to said oligonucleotide prior to administering the oligonucleotide.

2. The method of claim 1, wherein said activator is a 2'-5'-oligonucleotide.

3. The method of claim 2, wherein said activator comprises a 2',5'-oligoadenylate oligonucleotide.

4. The method of claim 3, wherein said 2',5'-oligoadenylate oligonucleotide is p5'A2'p5'A2'p5'A2'p5'A.

5. The method of claim 1, wherein said strand of RNA is mRNA.

6. The method of claim 1, additionally comprising the step of identifying a single stranded region of said strand of RNA to which said antisense moiety can bind or anneal.

7. The method of claim 1, wherein said strand of RNA is the RNA transcript of an oncogene or a proto-oncogene.

8. The method of claim 1, wherein said strand of RNA is the RNA transcript of a viral protein.

9. The method of claim 1, wherein said strand of RNA contained in said cell is the genome of an RNA virus.

10. The method of claim 1, wherein said oligonucleotide attached to an activator of 2-5A-dependent RNase is administered intravenously, topically, or by direct infusion into a desired tissue.

11. The method of claim 1, wherein said subject is human.

* * * * *